(12) United States Patent
Mojtabai

(10) Patent No.: US 9,606,127 B2
(45) Date of Patent: Mar. 28, 2017

(54) ORDERED TWO- AND THREE-DIMENSIONAL STRUCTURES OF AMPHIPHILIC MOLECULES

(71) Applicant: Fatemeh Mojtabai, Weston, MA (US)

(72) Inventor: Fatemeh Mojtabai, Weston, MA (US)

(*) Notice: Subject to any disclaimer, the term of this patent is extended or adjusted under 35 U.S.C. 154(b) by 0 days.

(21) Appl. No.: 14/609,767

(22) Filed: Jan. 30, 2015

(65) Prior Publication Data
US 2015/0338416 A1 Nov. 26, 2015

Related U.S. Application Data

(60) Continuation of application No. 12/901,244, filed on Oct. 8, 2010, now abandoned, which is a division of
(Continued)

(51) Int. Cl.
*G01N 33/68* (2006.01)
*B82Y 15/00* (2011.01)
(Continued)

(52) U.S. Cl.
CPC .......... *G01N 33/6845* (2013.01); *B82Y 15/00* (2013.01); *C07K 1/113* (2013.01); *B01J 2219/00317* (2013.01); *B01J 2219/00585* (2013.01); *B01J 2219/00596* (2013.01); *B01J 2219/00659* (2013.01); *B01J 2219/00725* (2013.01); *C07B 2200/11* (2013.01);
(Continued)

(58) Field of Classification Search
CPC ............. G01N 22/6845; G01N 2500/20; B01J 2219/00317; B01J 2219/00585; B01J 2219/00596; B01J 2219/0659; B01J 2219/00725; B82Y 15/00; C07B 2200/11; C07K 1/113; C40B 40/10; C40B 60/14
See application file for complete search history.

(56) References Cited

U.S. PATENT DOCUMENTS 4,489,133 A 12/1984 Kornberg
4,859,538 A 8/1989 Ribi
(Continued)

FOREIGN PATENT DOCUMENTS

EP 0274824 A1 7/1988
EP 0431400 A1 6/1991
(Continued)

OTHER PUBLICATIONS

"Growth and Isolation of Purple membrane", http://qsad.bu.edu/curriculum/labs/purplemembrane.html, (Mar. 21, 2005).
(Continued)

*Primary Examiner* — Jeremy C Flinders
(74) *Attorney, Agent, or Firm* — McCarter & English, LLP; Cristin H. Cowles; Anita M. Bowles

(57) ABSTRACT

The invention pertains, at least in part, to a method for forming an ordered structure of amphiphilic molecules, such as proteins. The method includes contacting a population of amphiphilic molecules with an interface; compressing said population laterally to an appropriate pressure, such that an ordered structure at the interface is formed. The invention also pertains to the two- and three-dimensional ordered structures that are formed using the planar membrane compression method of the invention.

10 Claims, 9 Drawing Sheets

Related U.S. Application Data application No. 10/003,468, filed on Oct. 23, 2001, now Pat. No. 7,820,597.

(60) Provisional application No. 60/242,913, filed on Oct. 24, 2000.

(51) Int. Cl.
    C07K 1/113    (2006.01)
    C40B 40/10    (2006.01)
    C40B 60/14    (2006.01)

(52) U.S. Cl.
    CPC .............. C40B 40/10 (2013.01); C40B 60/14 (2013.01); G01N 2500/20 (2013.01)

(56) References Cited

U.S. PATENT DOCUMENTS

| | | |
|---|---|---|
| 5,044,308 A | 9/1991 | Mojtabaj |
| 5,223,409 A | 6/1993 | Ladner et al. |
| 5,514,501 A | 5/1996 | Tarlov |
| 5,693,476 A | 12/1997 | Scheller |
| 5,970,381 A | 10/1999 | Ohno et al. |
| 6,763,149 B2 | 7/2004 | Riley et al. |
| 7,820,597 B2 | 10/2010 | Mojtabai |
| 2003/0082827 A1 | 5/2003 | Craig et al. |
| 2005/0112607 A1 | 5/2005 | Bamdad et al. |

FOREIGN PATENT DOCUMENTS

| | | |
|---|---|---|
| WO | 9509058 A2 | 4/1995 |
| WO | 9610178 A1 | 4/1996 |
| WO | 0004382 A1 | 1/2000 |

OTHER PUBLICATIONS

"Lecture 7: Membrane Structure", http://members.aol.com/BearFlag45/Biology1A/LectureNotes/lec07.html, (Mar. 21, 2005).
"The Shape Shifting Business," Nature Biotechnology, vol. 18:905 (2000).
"Ullmann's Encyclopedia of Industrial Chemistry," vol. A26, pp. 696, 706 (1995).
Amann, Egon, et al., "Tightly Regulated tac Promoter Vectors Useful for the Expression of Unfused and Fused Proteins in *Escherichia coli*," Gene, vol. 69:301-315 (1988).
Baldari, C., et al., "A Novel Leader Peptide Which Allows Efficient Secretion of a Fragment of Human Interleukin 1. beta. in *Saccharomyces cerevisiae*," The EMBO Journal, vol. 6(1):229-234 (1987).
Bell, Christine M., et al., "Materials Chemistry of Organic Monolayer Thin Films," Materials Chemistry: An Emerging Discipline, pp. 211-230 (1995).
Brisson, A., et al., "Quaternary Structure of the Acetylcholine Receptor," Nature, vol. 315:474-477 (1985).
Buck, Linda, et al., "A Novel Multigene Family May Encode Odorant Receptors: A Molecular Basis for Odor Recognition," Cell, vol. 65:175-187 (1991).
Burns, Mark A., et al., "An Integrated Nanoliter DNA Analysis Device," Science, vol. 282:484-487 (1998).
Cho, Charles Y., et al., "An Unnatural Biopolymer," Science, vol. 261:1303-1305 (1993).
Cornwell, Marilyn M., et al., "Increased Vinblastine Binding to Membrane Vesicles from Multidrug-resistant KB Cells," The Journal of Biological Chemistry, vol. 261(17):7921-7928 (1986).
Costello, M.J., et al., "Membranous Cytochrome c Oxidase, A Freeze-Fracture Electron Microscopic Analysis," J. Mol. Biol., vol. 162:131-156 (1982).
Craven, Bryan M., "Crystal Structure of Cholesterol Monohydrate," Nature, vol. 260:727-729 (1976).
Cull, Millard G., et al., "Screening for Receptor Ligands Using Large Libraries of Peptides Linked to the C Terminus of the lac Repressor," Proc. Natl. Acad. Sci. USA, vol. 89:1865-1869 (1992).
Cwirla, Steven E., et al., "Peptides on Phage: A Vast Library of Peptides for Identifying Ligands," Proc. Natl. Acad. Sci. USA, vol. 87:6378-6382 (1990).
Darst, Seth A., et al., "Two-dimentional Crystals of Streptavidin on Biotinylated Lipid Layers and Their Interactions with Biotinylated Macromolecules," Biophys. J., vol. 59:387-396 (1991).
Demel, R.A., et al., "Relation Between Various Phospholipase Actions on Human Red Cell Membranes and the Interfacial Phospolipid Pressure in Monolayers," Biochimica et Biophysica Acta, vol. 406:97-107 (1975).
Devlin, James J., et al., "Random Peptide Libraries: A Source of Specific Protein Binding Molecules," Science, vol. 249:404-406 (1990).
Dewitt, Sheila Hobbs, et al., "'Diversomers': An Approach to Nonpeptide, Nonoligomeric Chemical Diversity," Proc. Natl. Acad. Sci. USA, vol. 90:6909-6913 (1993).
Erb, Eric, et al., "Recursive Deconvolution of Combinatorial Chemical Libraries," Proc. Natl. Acad. Sci. USA, vol. 91:11422-11426 (1994).
Felici, Franco, et al., "Selection of Antibody Ligands from a Large Library of Oligopeptides Expressed on a Multivalent Exposition Vector," J. Mol. Biol., vol. 222:301-310 (1991).
Fodor, Stephen P.A., et al., "Multiplexed Biochemical Assays with Biological Chips," Nature, vol. 364:555-556 (1993).
Frey, Terrence G., "Cytochrome c Oxidase: Structural Studies by Electron Microscopy of Two-Dimensional Crystals," Microscopy Research and Technique, vol. 27:319-332 (1994).
Frey, Terrence G., et al., "Electron Microscopy of Cytochrome c Oxidase Crystals: Monomer-Dimer Relationship and Cytochrome c Binding Site," J. Mol. Biol., vol. 237:275-297 (1994).
Frey, Terrence G., et al., "Structure and Orientation of Cytochrome c Oxidase in Crystalline Membranes," The Journal of Biological Chemistry, vol. 253(12):4389-4395 (1978).
Fuller, S.D., et al., "Structure of Cytochrome c Oxidase in Deoxycholate-derived Two-dimensional Crystals," J. Mol. Biol., vol. 134:305-327 (1979).
Gallop, Mark A., et al., "Applications of Combinatorial Technologies in Drug Discovery. 1. Background and Peptide Combinatorial Libraries," Journal of Medicinal Chemistry, vol. 37(9):1233-1251 (1994).
Garavito, R. Michael, et al., "Crystallization of Membrane Proteins: A Minireview," Journal of Crystal Growth, vol. 110:89-95 (1991).
Garavito, R. Michael, et al., "The Art of Crystallizing Membrane Proteins," Methods in Enzymology, vol. 1(1):57-69 (1990).
Glaeser, Robert M., "Electron Crystallography of Biological Macromolecules," Ann. Rev. Phys. Chem., vol. 36:243-75 (1985).
Glaeser, Robert M., et al., "High-resolution Electron Crystallography of Protein Molecules," Ultramicroscopy, vol. 52:478-486 (1993).
Goeddel, David V., "Systems for Heterologous Gene Expression," Methods in Enzymology, vol. 185:3-7 (1990).
Gottesman, Susan, "Minimizing Proteolysis in *Escherichia coli*: Genetic Solutions," Methods in Enzymology, vol. 185:119-129 (1990).
Greer et al. Proc. Nati. Acad. Sci. USA, Jan. 1978, vol. 75, No. 1 pp. 303-507.
Hanggi-Mojtabai, Fatemeh, "Total Internal Reflection and Fluorescence Recovery after Photobleaching and Determination of Molecular Motion in Biological Membranes," Doctoral Thesis, University of Basel, Switzerland, pp. 61-63, 70-72 (1985).
Hemming SA, Bochkarev A, Darst SA, Kornberg RD, Ala P, Yang DS, Edwards AM., The mechanism of protein crystal growth from lipid layers., J Mol Biol. Feb. 17, 1995;246(2):308-16.
Henderson, R., et al., "Arrangement of Cytochrome Oxidase Molecules in Two-dimensional Vesicle Crystals," J. Mol. Biol., vol. 112:631-648 (1977).
Hirai, Hisamaru, et al., "A Novel Putative Tyrosine Kinase Receptor Encoded by the eph Gene," Science, vol. 238:1717-1720 (1987).

(56) References Cited

OTHER PUBLICATIONS

Hohenfeld et al. Purification of histidine tagged bacteriorhodopsin pharaonis halorhodopsin and pharaonis sensory rhodopsin II functionally expressed in *Escherichia coli*. FEBS Letters 442 (1999) 198-202.
Kornberg, Roger D., et al., "Two-dimensional Crystals of Proteins on Lipid Layers," Current Opinion in Structural Biology, vol. 1:642-646 (1991).
Koppenol et al. Engineering Two-Dimensional Protein Order at Surfaces. J. of Pharmaceutical Sciences. vol. 86, No. 11, 1997, 1204-1209.
KSV Instruments. http://www.ksvinc.com/LB.htm, (Mar. 18, 2005).
Kuhlbrandt, W., "Two-dimensional Crystallization of Membrane Proteins," Quarterly Reviews of Biophysics, vol. 25 (1)1-49 (1992).
Kurjan, Janet, et al., "Structure of a Yeast Pheromone Gene (MF. beta.): A Putative .beta.-Factor Precursor Contains Four Tandem Copies of Mature .beta.-Factor," Cell, vol. 30:933-943 (1982).
Lam, Kit S., "Application of Combinatorial Library Methods in Cancer Research and Drug Discovery," Anti-Cancer Drug Design, vol. 12:145-167 (1997).
Lam, Kit S., et al., "A new type of synthetic peptide library for identifying ligand-binding activity," Nature, vol. 354:82-84 (1991).
Luckow, Verne A., et al., "High Level Expression of Nonfused Foreign Genes with Autographa californica Nuclear Polyhedrosis Virus Expression Vectors," Virology, vol. 170:31-39 (1989).
Marx, Jean, et al., "Bad for the Heart, Bad for the Mind?" Science, vol. 294:508-509 (2001).
McConnell, Harden M., "Structures and Transitions in Lipid Monolayers at the Air-Water Interface," Annu. Rev. Phys. Chem., vol. 42:171-95 (1991).
Mimms, Larry T., et al., "Phospholipid Vesicle Formation and Transmembrane Protein Incorporation Using Octyl Glucoside," Biochemistry, vol. 20:833-840 (1981).
Moy, V.T. et al. "Molecular Order in Finite Two-dimensional Crystals of Lipid at the Air-Water Interface," J. Phys. Chem., vol. 92:5233-5238 (1988).
Nacro et al., "Conformationally Constrained Analogues of Diacylglycerol (DAG). 16.1 How Much Structural Complexity Is Necessary for Recognition and High Binding Affinity to Protein Kinase C?", 2000, Journal of Medicinal Chemistry, vol. 43, No. 5, pp. 921-944.
Newman, Richard H., "Two-dimensional Crystallization of Proteins on Lipid Monolayers," Electron Microsc. Rev., vol. 4:197-203 (1991).
Ohlsson et al. (Bioelectrochemistry and Bioenergetics (1995) vol. 38, pp. 137-148).
Pattus, F. et al. "Spreading of Biomembranes at the Air/Water Interface," Biochimica et Biophysica Acta, vol. 57:71-82 (1978).
Perrimon, Norbert, "Signalling Pathways Initiated by Receptor Protein Tyrosine Kinases in *Drosophila*," Current Opinion in Cell Biology, vol. 6:260-266 (1994).
Plowman, Gregory D., et al., "Ligand-specific Activation of HER4/p180.sup.erbB4, a Fourth Member of the Epidermal Growth Factor Receptor Family," Proc. Natl. Acad. Sci. USA, vol. 90:1746-1750(1993).
Rein ten Wolde, Pieter, et al., "Enhancement of Protein Crystal Nucleation by Critical Density Fluctuations," Science, vol. 277:1975-1978 (1997).
Rosenberg, Mark F., et al., "Structure of the Multidrug Resistance P-glycoprotein to 2.5 nm Resolution Determined by Electron Microscopy and Image Analysis," The Journal of Biological Chemistry, vol. 272(16)10685-10694 (1997).
Schultz, Loren D., et al., "Expression and Secretion in Yeast of a 400-kDa Envelope Glycoprotein Derived from Epstein-Barr Virus," Gene, vol. 54:113-123 (1987).
Schwarz, Herbert, et al., "A Receptor Induced by Lymphocyte Activation (ILA): A New Member of the Human Nerve-Growth-Factor/Tumor-Necrosis-Factor Receptor Family," Gene, vol. 134:295-298 (1993).
Scott, Jamie K., et al., "Searching for Peptide Ligands with an Epitope Library," Science, vol. 249:386-390 (1990).
Shieh, H.S., et al., "Crystal Structure of Anhydrous Cholesterol," Nature, vol. 267:287-289 (1977).
Shier, Peter, et al., "Primary Structure of a Putative Receptor for a Ligand of the Insulin Family," The Journal of Biological Chemistry, vol. 264(25):14605-14608 (1989).
Shinzawa-Itoh, Kyoko, et al., "Effects of Ethyleneglycol Chain Length of Dodecyl Polyethyleneglycol Monoether on the Crystallization of Bovine Heart Cytochrome c Oxidase," J. Mol. Biol., vol. 246:572-575 (1995).
Smith, Gale E., et al., "Production of Human Beta Interferon in Insect Cells Infected with a Baculovirus Expression Vector," Molecular and Cellular Biology, vol. 3(12):2156-2165 (1983).
Sonveaux, Nathalie, et al., "Secondary and Tertiary Structure Changes of Reconstituted P-glycoprotein," The Journal of Biological Chemistry, vol. 271(40):24617-24624 (1996).
Studier, F., William, et al., "Use of T7 RNA Polymerase to Direct Expression of Cloned Genes," Methods in Enzymology, vol. 185:60-89 (1990).
Tsukihara, Tomitake, et al., "Structures of Metal Sites of Oxidized Bovine Heart Cytochrome c Oxidase at 2.8 .ANG." Science, vol. 269:1069-1074 (1995).
Valpuesta, J.M., et al., "Electron Cryo-microscopic Analysis of Crystalline Cytochrome Oxidase," J. Mol. Biol., vol. 214:237-251 (1990).
Vanderkooi, G., et al., "Biological Membrane Structure: III. The Lattice Structure of Membranous Cytochrome Oxidase," Biochimica et Biophysica Acta, vol. 274:38-48 (1972).
Verclas et al., X-ray diffraction from a single layer of purple membrane at the air/water interface., J Mol Biol. Apr. 16, 1999;287(5):837-43.
Verger, R., et al., "Spreading of Membranes at the Air/Water Interface," Chemistry and Physics of Lipids, vol. 16:285-291 (1976).
Wada, Ken-nosuke, et al., "Codon Usage Tabulated from the GenBank Genetic Sequence Data," Nucleic Acids Research, vol. 20:2111-2118 (1992).
Weis, Robert M., et al., "Two-dimensional Chiral Crystals of Phospholipid," Nature, vol. 310:47-49 (1984).
Wong, Stanislaus S., et al., "Covalently Functionalized Nanotubes as Nanometre-sized Probes in Chemistry and Biology," Nature, vol. 394:52-55 (1998).
Yoshikawa, Shinya, et al., "Strategies for Crystallization of Large Membrane Protein Complexes," Journal of Crystal Growth, vol. 122:298-302 (1992).
Zuckerman, Ronald N., et al., "Discovery of Nanomolar Ligands for 7-Transmembrane G-Protein-Coupled Receptors from a Diverse N-(Substituted)glycine Peptoid Library," J. Med. Chem., vol. 37:2678-2685 (1994).

© 2002 Fatemeh Mojtabai

© 1994 American Chemical Society

© 2002 Fatemeh Mojtabai

© 1994 American Chemical Society

© 2002 Fatemeh Mojtabai

© 1994 Wiley-Liss, Inc.

ORDERED TWO- AND THREE-DIMENSIONAL STRUCTURES OF AMPHIPHILIC MOLECULES

RELATED APPLICATIONS

This application is a continuation of U.S. application Ser. No. 12/901,244, filed Oct. 8, 2010, which is a divisional of U.S. application Ser. No. 10/003,468, filed Oct. 23, 2001, which claims priority to U.S. Provisional Patent Application Ser. No. 60/242,913, entitled "Controlled Fabrication of Crystals and Long-Range Ordered Arrays of Membrane Proteins for High Throughput Structure Analysis and Screening Applications," filed on Oct. 24, 2000; the entire contents of any patents, patent applications, and references cited throughout this specification are hereby incorporated by reference in their entireties.

AUTHORIZATION TO USE COPYRIGHT MATERIAL PURSUANT TO 37 CFR 1.171(e)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Protein structure information is indispensable for the design of effective drugs. Designers need detailed structures of proteins, to atomic resolution, so that they can tailor their drugs to interact with specific target areas in a protein molecule. Conventionally, x-ray crystallography has been used to elucidate the three-dimensional (3-D) structure of proteins. This technique can accurately identify the location of atoms by diffracting x-rays from innumerable protein molecules stacked up in an ordered form, so called "crystal". However, crystallographers have yet to overcome the fact that most proteins do not readily form ordered assemblies. Particularly important but extremely difficult to crystallize are membrane proteins. Membrane proteins are not soluble, therefore conventional three-dimensional crystallization techniques usually do not work for them.

To date, the number of transmembrane proteins crystallized remains small. Indeed, recently it was noted that only 26 out of the approximately 1000 protein structure holdings in the Protein Data Bank (PDB) are membrane proteins (*Nature Biotechnology* 905 (2000)). In a 1998 report of the Committee for the National Magnetic Resonance Collaboration, it was stated that "even though membrane proteins represent 30% of the proteome, relatively little is known about the structure of these proteins, because of their resistance to crystallization."

In general, membrane proteins are comprised of hydrophobic portions within their transmembrane regions, which render them insoluble in water.

Consequently, unlike soluble proteins, membrane proteins do not form the monodispersed, isotropic solutions needed to grow crystals. This accounts for the near absence of structure information in PDB for transmembrane portions of most membrane proteins. In contrast, extracellular domains of membrane proteins which lack the hydrophobic regions, have been successfully crystallized.

A few techniques have been developed for membrane protein crystallization (Garavito, R. M. & Picot, D. *Methods* 1, 57-69 (1990); Kuelbrandt, W. Q. *Rev. Biophysics* 25, 1-49 (1992)). These techniques include i) application of conventional three-dimensional crystallization techniques directly to a preparation of detergent-solubilized membrane protein, e.g., by adding precipitation agents like ammonium sulfate or polyethylene glycol; and (ii) reconstitution of membrane proteins into lipid bilayers by detergent removal. In both of these methods, the crystallization process is hindered by the presence of detergent. For example, the detergent may inhibit crystal nucleation and growth. The presence of the detergent may require time-consuming and exhaustive detergent screening to determine whether the solubilized protein is functionally active. Furthermore, the crystals may include the detergent, therefore different detergents may yield different crystals of the same protein. Detergents also may effect protein orientation; i.e. alternating molecules face up or down or two layers stack up with an in plane axis of two-fold symmetry. Furthermore, the processes involving detergents are tedious and require long crystallization times, (e.g., typically several days to several weeks). In addition, these methods require large quantities (several 100 milligrams to grams) of purified protein that is not easily available in most cases. Also, designing crystallization experiments for a new system is not straight forward, as the same protocol does not always work for other systems.

Recently Landau and Rosenbusch demonstrated formation of three-dimensional crystals of bacteriorhodopsin by emulating the natural environment of the membrane protein in bicontinuous lipidic cubic phases (Landau, E. M. & Rosenbusch, J. P. *Proc. Natl. Acad. Sci. USA* 93, 14532-14535 (1996)). Their method included a protein delipidation process and required the use of detergents and precipitants. The crystals produced by this method were small, 20-40 µm in diameter and 5 µm thick, but diffracted x-rays from an intense microbeam source to 2.5 A resolution. These harsh conditions may adversely affect the structure and function of more vulnerable membrane proteins. Furthermore, their method requires designing and building an artificial membrane with a different lattice size for each membrane protein. This does not appear to be an easy task.

Planar biological membranes are becoming of increasing interest because they provide a natural fluid membrane milieu that is critically important to the function of membrane proteins. This environment is ideal for immobilizing proteins under nondenaturing conditions and in a well-defined orientation. Two-dimensional crystallization of soluble proteins on lipid monolayers has been attempted for several systems (Kornberg, R. D. & Darst, S. A. *Curr. Opinion in Struct. Biol.* 1, 642-646 (1991); Newman, R. *Electron Microscopy Reviews* (1991)). Formation of two-dimensional crystals of non-soluble integral membrane proteins by compression of a monolayer at an air-water interface, has not yet been explored. Glaeser demonstrated preparation of thin, flat electron microscopy specimen from monolayers spread at the air-water interface of a monolayer trough, from native purple membranes including naturally occurring two-dimensional crystals of bacteriorhodopsin (Glaeser, R. A. *Ann. Rev. Phys. Chem.* 36, 243-75 (1985)).

In phospholipid systems, finite two-dimensional domains have been produced by monolayer compression at an air-water interface for several lipids. In studies concerning the compression of the lipid DPPC in monolayers, the presence of long-range orientational order throughout the solid domains produced at the coexistence region between two phases was found (Moy, V. T. et al. *J. Phys. Chem.* 92, 5233

(1988)). The experimental approach used in these studies does not provide concrete evidence on the crystalline order of the solid domains. However, the evidence of this long-range orientational order together with theoretical analysis of structure formation in lipid monolayers may provide a basis for understanding the production of structures in more complex mixed lipid-protein monolayer systems (McConnell, H. M. *Annu. Rev. Phys. Chem.* 42, 171-95 (1991)).

SUMMARY OF THE INVENTION

The invention pertains, at least in part, to a new, simple and fast method for the fabrication of ordered structures, e.g., ordered two- and three-dimensional crystals, of amphiphilic molecules, such as but not limited to proteins, e.g., membrane proteins. Unlike conventional techniques, the methods of the invention allow for variation of the experimental parameters to facilitate fabrication of ordered structures with both long- as well as short-range orientation order, suitable for imaging techniques, such as high-resolution crystallographic analysis. In addition, the method is several times faster than conventional techniques, and maintains the native asymmetry of the amphiphilic molecule. The methods of the invention provide a general approach for crystallizing amphiphilic molecules such as membrane proteins. This is of considerable research interest since membrane proteins comprise a high proportion of pharmaceutically relevant targets. Yet the difficulties involved in crystallizing membrane proteins by using conventional techniques has posed a serious problem in the area of drug discovery. The present invention may lead to new discoveries of significant biotechnological importance.

In an embodiment, the invention pertains, at least in part, to a method for forming an ordered structure of amphiphilic molecules. The method includes contacting a population of amphiphilic molecules with an interface; compressing said population laterally to an appropriate pressure, such that an ordered structure at the interface is formed.

In a further embodiment, the invention pertains to two-dimensional ordered structures, which are comprised of a population of amphiphilic molecules. The invention also pertains to three-dimensional ordered structures which are formed by planar membrane compression, e.g., by contacting a population of amphiphilic molecules with an interface; and compressing the population to an appropriate pressure, such that a three-dimensional ordered structure is formed.

The invention also pertains, at least in part, to methods for screening a test compound. The method includes contacting the test compound with at least a portion of an ordered structure; and analyzing the results of the interaction of the test compound and the ordered structure, such that said test compound is screened.

The invention also pertains, at least in part, to a method for the discovering new leads. The method includes development of novel high throughput screening systems based on structure-activity relationships. The method comprises a rapid fluorescence imaging method to probe the molecular outline of membrane proteins at low-resolutions (somewhat comparable to that obtained from an electron diffraction projection data at around 10-25 Å). This low-resolution imaging technique can be used as a powerful tool to not only probe the morphology of a protein but to also depict probe changes in its conformation or degree of aggregation as a result of its interaction with other molecules. This is of relevance in biological molecular recognition events. A specific implication of this technique is, for example, in signal transduction, where binding of molecular messengers to cell receptors, initiates a series of complex events that generally include a change in conformation or multimerization, e.g., dimerization, of the protein.

The invention also pertains, at least in part, to a method for determining the shape of an amphiphilic molecule. The method includes contacting a population of the molecule with an interface; compressing the population to an appropriate pressure, such that an ordered structure is formed, and analyzing the ordered structure such that the shape of the amphiphilic molecule is determined.

A further application of the technology to probe structure information at atomic scale resolutions is also presented. Structure information at atomic resolution is indispensable for elucidation of the mechanism of action of key membrane protein targets. Such information is crucial to a better understanding of the nature of disease and subsequently to developing more effective drugs.

In another embodiment, the invention pertains, at least in part, to a method for fabricating an ordered structure of a protein. The method includes expressing a protein in a cell, obtaining the protein from the cell, applying said protein to an interface, and compressing the protein on the interface to an appropriate pressure.

In another embodiment, the invention includes a method for determining the structure of a protein. The method includes expressing the protein in a cell, obtaining the protein from the cell, applying said protein to an interface, compressing said protein on said interface to an appropriate pressure, such that an ordered structure of said protein is formed, and analyzing said ordered structure such that the structure of said protein is determined.

The invention also pertains to a protein chip. The chip includes a plurality of ordered structures in discrete wells, which are fabricated by planar membrane compression.

In one embodiment, the invention pertains to methods for forming ordered structures of amphiphilic molecules on an interface in a fast and controlled fashion. The methods may be performed using an apparatus with an integrated with real-time digital imaging laser fluorescence microscopy to allow for in-situ characterization of structure formation, throughout the fabrication process. The use of a robotics film transfer facilitates preparation of specimens for use in atomic resolution measurements such as electron-, x-ray crystallography as well as scanning probe microscopy.

The inventions also pertains, at least in part, to a system for forming and analyzing a ordered structure of an amphiphilic molecules on an interface. The system includes a trough comprising a frame having top and bottom separable frame portions, a plate for holding an interface disposed within said frame and including a substantially transparent portion; a seal assembly for sealing the subphase from the frame, and a movable barrier for laterally compressing a population of amphipilic molecules deposited on said subphase to form an ordered structure; and an image acquisition and processing system coupled to the trough for imaging the ordered structure on the plate.

In yet another embodiment, the invention pertains, at least in part, to a system for forming an ordered structure of an amphiphilic molecule on a subphase. The system includes a trough comprising a frame having top and bottom separable frame portions, a plate disposed within said frame and including a transparent portion; a seal assembly for preventing the subphase from reaching the frame, and a movable barrier for laterally compressing a population of the amphiphilic molecules deposited on said subphase to form said ordered structure; and a housing enclosing the trough; and a temperature control system for controlling the temperature within the trough.

In yet another further embodiment, the invention also pertains to a computer-readable medium for use in a system for forming and analyzing an ordered structure. The computer readable medium includes instructions for performing the computer implemented steps of: viewing an ordered structure formed by compression; and displaying an image of the ordered structure.

In yet another further embodiment, the invention also includes a trough for forming and analyzing an ordered structure. The trough includes a frame having top and bottom separable frame portions, a plate for holding a subphase disposed within said frame and having an array of microwells formed thereon for holding an array of ordered structures of membrane proteins; a seal assembly for sealing the subphase from the frame, and a movable barrier for laterally compressing a layer of amphipilic solution deposited on said subphase to form an ordered structure.

The methods and ordered structures of the invention provide many present and potential applications, which range from fields such as microelectronics to biotechnology, agriculture, and food as well as for development of cosmetics, home and personal care products. Specifically, in biotechnology the invention has potential for developing more effective therapeutic treatments. Other applications include discovery of active ingredients for use in food, cosmetics, home and personal care products. In agriculture, the methods of the invention may be used to design more effective herbicides and insecticides.

BRIEF DESCRIPTION OF THE DRAWINGS

FIG. 1b is a cross-sectional view of the plate of FIG. 1a.

DETAILED DESCRIPTION OF THE INVENTION

Figure 1A:
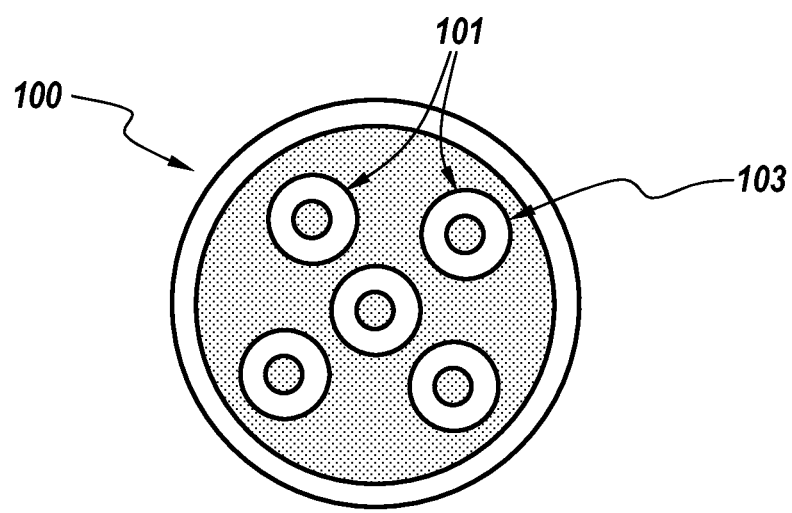
FIG. 1a is a top view of a plate mounted in a trough of the illustrative embodiment for developing discrete high-density protein arrays according to the teachings of the invention.

One of the fastest-growing branches of materials chemistry is in the area of planar mono- and multilayer films (Bell, C M. et al. *Materials Chemistry of Organic Monolayer and Multilayer Thin Films* (American Chemical Society, 1995)). The invention pertains, at least in part, to a rapid process for controlled fabrication of ordered structures by compression of a layer, e.g., a monolayer, of amphiphilic molecules toward and beyond a critical density point. Experiments have been conducted on three different model systems to elucidate application of the technology toward formation of two-dimensional as well as three-dimensional ordered structures for: (1) the cytochrome c oxidase (COX), (2) the multidrug resistance P-glycoprotein (P-gp), both large membrane spanning proteins having over 400 atoms and (3) cholesterol, a small amphiphilic molecule. The results provide direct visual evidence for the formation of interesting two-dimensional as well as three-dimensional ordered structures. Specifically, the two-dimensional ordered structures of cholesterol exhibit electron diffraction characteristics of highly ordered two-dimensional crystals. The diffraction pattern yields structure information to atomic resolution consistent with known data of cholesterol monohydrate crystals prepared by conventional methods (Craven, B. M. *Nature* 260, 727-729 (1976)). Furthermore, these studies reveal a direct correlation between the degree of supersaturation in two-dimensions, beyond a metastable critical density point, and the cholesterol crystal nucleation process. The methods of the invention provide a two-dimensional framework for studying the underlying effects promoting crystal nucleation process near a critical density point.

Digital fluorescence image analysis of the large two-dimensional ordered structures of the membrane proteins COX and Pgp provide interesting unexpected insight into the long-range orientational order of protein molecules. These protein ordered structures exhibit a remarkable long-range orientational order. The overall morphology of the ordered structures often resembles the known structure of individual protein molecules in their monomer or dimer forms. The structural information provided by using this technique is somewhat comparable to that obtained from low-resolution electron projection data around 10-25 Å.

1. Methods for Forming Two- and Three- Dimensional Ordered Structures

In one embodiment, the invention includes methods for forming ordered structures. The methods include contacting a population of amphiphilic molecules with an interface, compressing said population to an appropriate pressure, such that an ordered structure is formed. In a further embodiment, the structure of the ordered structures may be elucidated using imaging techniques.

In comparison to conventional techniques of three dimensional crystallization, the methods of the invention are simple, fast (several minutes vs. days and months) and require only a small amount of material (a fraction of a milligram vs. grams of the protein). In addition, the amphiphilic molecules can be ordered in theirs natural environment without using detergents or solubilizing agents. For example, it is believed that in its natural environment the an amphiphilic molecule, such as a protein, is more likely to resume its function as well as its native conformational state, than it would in a solubilized or reconstituted form. Furthermore, the methods of the invention do not require the use of a highly purified protein. Instead, the process can be adapted to form ordered structures of amphiphilic molecules, such as proteins, from small quantities of a crude preparations, such as crude membrane preparations. This is of considerable advantage for membrane proteins, since most membrane proteins are not readily available in large quantities and it is even more difficult to find them in a purified form. However, for those proteins whose genes are known, small quantities of a crude membrane form may be prepared, by overexpressing the protein in cell cultures. It is anticipated that by overcoming the limitations imposed by conventional methods, this unique and simple approach has the clear potential to be adopted as a general means to produce ordered structures of amphiphilic molecules, such as membrane proteins, in a fast and cost-effective manner.

The term "ordered structures" includes ordered arrays and crystalline arrays of amphiphilic molecules. The ordered structures may be two dimensional (e.g., a single layer of amphiphilic molecules) or three dimensional (e.g., two or more layers of amphiphilic molecules). Ordered structures can be analyzed by imaging techniques known in the art. In an embodiment, the ordered structures may be crystalline, and can be analyzed by appropriate imaging or diffraction techniques, e.g., electromagnetic radiation diffraction, to determine the shape or structure of the amphiphilic molecule. The term includes nano structures and micro structures. The term includes both three-dimensional and two-dimensional crystals. In an embodiment, the ordered structure is comprised of a population of similar, advantageously identical, molecules.

The term "imaging" or "imaging techniques" includes methods known in the art using any form of electromagnetic radiation, neutrons, including techniques such as absorption, fluorescence, reflectance, diffraction, scattering and includes illumination techniques such as transmission, reflectance, incident-light fluorescence, confocal, evanescent wave (including total internal reflection fluorescence and surface plasmon resonance), near field, multi-photons, interference, polarized light, chemi-luminescence and scanning probe microscopy techniques such as confocal, atomic force and tunneling.

The term "crystalline array" includes arrays which diffract electromagnetic radiation, e.g., x-rays, neutrons, light, etc. Crystalline arrays can be either two- or three-dimensional.

The term "diffraction of electromagnetic radiation" includes to diffraction by any source of radiation known to those in the art, such as, but not limited to, neutrons, electromagnetic waves such as X-rays, electrons introduced from an x-ray tube, and focused and collimated beams of a synchrotron source or an electron microscope. The term also includes the reflection of the primary radiation by sets of parallel planes within the unit cells of a crystal. For example, when a beam of radiation shines on a crystal, it is scattered by the atoms in all directions. In certain directions, these scattered rays reinforce each other and add up to a diffracted beam.

The term "ordered array" includes arrays in which amphiphilic molecules assume the same orientation within the array. Ordered arrays can be either two or three dimensional.

The term "amphiphilic molecules" includes proteins, lipids, lipoproteins, steroids, cholesterol, or other molecules or derivatives thereof which can be applied to an interface, compressed, to yield an ordered structure. In certain embodiments, the term amphiphilic molecules do not include lipids.

The term "protein" includes both naturally occurring, mutant, modified, and labeled (e.g., polypeptides. The protein may be comprised of at least one hydrophobic region on its surface. The protein is not water soluble. In a further embodiment, the protein may be a membrane protein, and/or a cellular receptor.

The term "membrane protein" includes proteins which in their native state are associated with lipid membranes (e.g., nuclear membrane, cellular membrane, mitochondrial membranes, liposomal membranes, endoplasmic reticulum membranes, chloroplast membranes, etc.). The term includes transmembrane proteins, and proteins which are partially or fully embedded in membranes in their native state. Examples of membrane proteins include G-protein coupled receptors (GPCRs), signal transduction receptors, orphan receptors, and other cellular receptors.

The term "membrane proteins" include both extrinsic and intrinsic proteins. Extrinsic membrane proteins are generally located entirely outside of the membrane, but are bound to the membrane by weak molecular attractions (such as, for example, ionic, hydrogen, and/or Van der Waals bonds). Intrinsic membrane proteins are, generally, embedded in the membrane. Intrinsic membrane proteins include, but are not limited to proteins which extend from one side of the membrane to the other, i.e., transmembrane proteins. Examples of transmembrane proteins include, ion channels and ion pumps. The term also includes glycoproteins which comprise carbohydrate sugars covalently attached to the protein. A typical mammalian cell may have several hundred distinct types of glycoprotein studding its plasma membrane.

Membrane proteins may comprise single transmembrane domains involves certain membrane proteins that have multiple transmembrane domains. A commonly used type of structure seen in many hundreds of serpentine transmembrane proteins involves 7 hydrophobic domains inserted into the plasma membrane separated by hydrophilic regions that are looped out alternatively into either the cytoplasm or the extracellular space.

In one embodiment, the proteins of the invention include receptors. There are three general classes of cell-surface receptors based on their mechanism of signal transduction; i.e. (1) ion-channel linked receptors, (2) enzyme-linked/catalytic receptors and (3) G protein-coupled receptors involving second messenger molecules. These last two classes of receptor molecules have an extracellular domain that recognizes a specific molecular signal (e.g., such as a cytokine), and a transmembrane domain that produces a response.

The term "receptor protein" or "receptor" includes any receptor which interacts with an extracellular molecule (i.e. hormone, growth factor, peptide) to modulate a signal in the cell. To illustrate the receptor can be a cell surface receptor, or in other embodiments can be an intracellular receptor. In preferred embodiments, the receptor is a cell surface receptor, such as: a receptor tyrosine kinase, e.g., an EPH receptor; an ion channel; a cytokine receptor; an multisubunit immune recognition receptor, a chemokine receptor; a growth factor receptor, or a G-protein coupled receptor, such as a chemoattracttractant peptide receptor, a neuropeptide receptor, a light receptor, a neurotransmitter receptor, or a polypeptide hormone receptor.

At least four families of hormone receptors can be defined on the basis of similarity in primary sequence, predicted secondary and tertiary structure and biochemical function. These are the haemopoietin/interferon receptor family, the receptor kinase family, the tumor necrosis factor (TNF)/nerve growth factor (NGF) receptor family and the family of G-protein coupled, seven membrane-spanning receptors. Also included are orphan receptors for which no ligands have yet been identified.

In one embodiment, the membrane proteins of the invention are involved in signal transduction pathways. Signal transduction by growth factors, hormones and neurotransmitters is initiated by ligand binding to receptors located in the plasma membrane. The cell surface receptor responds to its specific ligand by a change in its conformation (such as the case of the G protein-coupled receptor beta adrenergic receptor) or by an induced dimerization (as in receptor dimerization in the case of the human growth factor receptors), multimerization or through formation of heteromeric complexes (as in the TGF β signaling through formation of types I and II serine/threonine kinase receptors).

Other proteins which can be used in the methods of the invention include proteins of the haemopoietin/interferon receptor family (e.g., type I transmembrane glycoproteins). Ligands that interact with these receptors include interferons (IFNs)-α, -β, and -γ, interleukins (IL)-2, -3, -4, -5, -6, -7, -9, -10, -11, -13, leukaemia inhibitory factor (LIF), oncostatin-M (OSM), erythropoitin (EPO), ciliary neurotrophic factor (CNTF), growth hormone and prolactin. Homodimerization appears to be an important feature of some cytokine receptors including those for growth hormone, prolactin, EPO and granulocyte colony-stimulating factor. Other proteins which also may be used include members of the TNF/NGF receptor family, such as those which have been identified as type I and type II TNF receptors, as well as the p75 subunit of the NGF receptors. The ligands for the TNF/NGF family members exist as type II transmembrane proteins, as well as secreted regulators.

Other membrane proteins include ligand-gated ion channels, such as neurotransmitter receptors (e.g., acetylcholine receptors, glutamate receptors, γ-aminobutyric acid (GABA) receptors, and glycine receptors). Other cellular receptors which can be used include, but are not limited to, enzyme-linked/catalytic receptors which have enzymic activity (e.g., a tyrosine-specific protein kinase such as the insulin receptor). The proteins of the invention include proteins of the five known classes of enzyme-linked/catalytic receptors: (1) receptor tyrosine kinases, which phosphorylate specific tyrosine residues on intracellular signaling proteins; (2) tyrosine kinase-associated receptors such as the prolactin and growth hormone receptors, which associate with proteins that have tyrosine kinase activity; (3) receptor tyrosine phosphatases, which remove phosphate groups from tyrosine residues of specific intracellular signaling proteins; (4) transmembrane receptor serine/threonine kinases, which add a phosphate group to serine and threonine side chains on target proteins; and (5) transmembrane guanyl cyclases, which catalyze the production of cyclic GMP in the cytosol. Tyrosine kinase domains are involved in a variety of diverse biological processes including cell growth, shape, cycle, transcription and apoptosis (programmed cell death).

The term "orphan receptors" include receptors with no known ligand and, in certain embodiments, obscure biological function. Receptors of all types comprise this large family. A large number of orphan receptors have been identified in the EPH family (Hirai et al (1987) *Science* 238:1717-1720). HER3 and HER4 are orphan receptors in the epidermal growth factor receptor family (Plowman et al. (1993) *Proc. Natl. Acad. Sci. USA* 90:1746-1750). ILA is a newly identified member of the human nerve growth factor/tumor necrosis factor receptor family (Schwarz et al. (1993) *Gene* 134:295-298). IRRR is an orphan insulin receptor-related receptor which is a transmembrane tyrosine kinase (Shier et al. (1989) *J. Biol Chem* 264:14606-14608). Several orphan tyrosine kinase receptors have been found in *Drosophila* (Perrimon (1994) *Curr. Opin. Cell Biol.* 6:260-266). Known orphan receptors include the nuclear receptors COUP-TF1/EAR3, COUP-TF2/ARP1, EAR-1, EAR-2, TR-2, PPAR1, HNF-4, ERR-1, ERR-2, NGFIB/Nur77, ELP/SF-1 and MPL (Parker et al, supra, and Power et al. (1992) *TIBS* 13:318-323).

One large subgroup of orphan receptors are found in the G protein coupled receptor family. Approximately 100 such receptors have been identified by function and these mediate transmembrane signaling from external stimuli (vision, taste and smell), endocrine function (pituitary and adrenal), exocrine function (pancreas), heart rate, lipolysis, and carbohydrate metabolism. Structural and genetic similarities suggest that G protein-coupled receptor superfamily can be subclassified into five distinct groups: (i) amine receptors (serotonin, adrenergic, etc.); (ii) small peptide hormone (somatostatin, TRH, etc.); (iii) large peptide hormone (LH-CG, FSH, etc.); (iv) secretin family; and (v) odorant receptors (Buck L. and Axel, R. (1991) *Cell* 65:175-187), with orphan receptors apparently occurring in each of the sub-families.

Examples of G protein coupled receptors ("GPCRs") include α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor, fMLP-like receptor, angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, Interleukin 8 (IL-8) IL-8RA, IL-8RB, Delta Opioid receptor, Kappa Opioid receptor, mip-1/RANTES receptor, Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor.

Examples of membrane proteins include G Protein-Coupled Receptors (GPCRs), which constitute one of the largest superfamilies of proteins. The transmembrane region of the GPCRs contain seven helices each spanning the lipid bilayer of the plasma membrane. When bound to specific ligands, signals transmitted to the intracelluar domain of these receptors are amplified by a family of heterotrimeric guanine nucleotide-binding proteins (G proteins). G proteins act as molecular switches that are activated by binding GTP and are inactivated when the GTP is hydrolyzed to GDP. The heterotrimeric G proteins consist of an $\alpha$, $\beta$, and $\gamma$ subunits.

GPCRs play key roles in a large number of pathophysiological conditions and trigger several important physiological responses, including vision, smell, and stress. They are targets of numerous therapeutic drugs, including the nonselective $\alpha$- and $\beta$-adrenergic agonists and antagonists, histamine antagonists, angiotensin antagonists, and serotonin antagonsists. The human genome is estimated to consist of over 1,000 GPCR genes. In addition, the human genome contains numerous genes for different $\alpha$, $\beta$, and $\gamma$ subunits to allow for the formation of hundreds of different G proteins. Consequently, there is a very large number of possible combinations of these receptors and G proteins, which provide the potential for development of a variety of clinically useful drugs.

Currently high-resolution structures are not available for any GPCR; although the structure of rhodopsin has been determined by electron crystallography. Metal binding sites can provide information about GPCR structure and activity or the dynamic conformational changes that accompany receptor activation. Detailed knowledge about the molecular structure of GPCRs is likely lead the development of new drugs with increased specificity for distinct receptor subtypes and/or signal transduction pathways.

Examples of physiological processes mediated by G proteins include glycogen breakdown, visual excitation, histamine secretion in all allergic reactions, control of the rate of the heartbeat led by stimulus such as epinephrine, light, IgE-antigen complexes, acetylcholine. These stimulant bind/affect the beta-adrenergic receptor, rhodopsin mast cell IgE receptor, and muscarinic receptor respectively.

Examples of EPH receptors include eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, mykl, myk2, ehkl, ehk2, pagliaccio, htk, erk and nonreceptors.

In another embodiment the receptor is a multisubunit receptor. Receptors can be comprised of multiple proteins referred to as subunits, one category of which is referred to as a multisubunit receptor is a multisubunit immune recognition receptor (MIRR). MIRRs include receptors having multiple noncovalently associated subunits. MIRRs can include, but are not limited to, B cell antigen receptors, T cell antigen receptors, Fc receptors and CD22. One example of an MIRR is an antigen receptor on the surface of a B cell. The MIRR on the surface of a B eel] comprises membrane-bound immunoglobulin (mIg) associated with the subunits Ig-$\alpha$ and Ig-$\beta$ or Ig-$\gamma$, which forms a complex capable of regulating B cell function.

The term "population" includes two or more amphiphilic molecules which are structurally similar or identical, such that diffraction techniques can be used to determine the structure of the amphiphilic molecules. In an advantageous embodiment, the population is comprised of identical amphiphilic molecules.

The term "appropriate pressure" includes the amount of pressure necessary for a particular protein to form a desired ordered structure, e.g., two dimensional or three dimensional ordered structure. In three dimensions, crystallization is promoted in a super-saturated solution. In two-dimensions, super-saturation translates into an increase in the lateral packing density of the molecules beyond a critical density point. The Langmuir technique is used to organize the molecules at an air-aqueous interface and subsequently compress them in two-dimensions to and beyond a critical density point. Examples of appropriate pressures include the pressures below the critical point for two-dimensional ordered structures and pressures at and above the critical density point for three-dimensional ordered structures. For example, in an embodiment, the population of amphiphilic molecules are compressed towards and beyond a critical density point, forming two different groups of protein domains. Large (200-500 $\mu$m) ordered structures are observed at intermediate packing densities, below the critical point. At higher packing densities, beyond the critical density point, formation of smaller (20-50 $\mu$m) ordered structures with a typical appearance of a three dimensional crystal, may be observed using appropriate techniques, e.g., fluorescence. Preferably, the pressure is applied laterally (e.g., essentially parallel to the plane of the interface) such that a ordered structure is formed.

The population of amphiphilic molecules may be compressed by any method, such that an ordered structure is formed. In certain embodiments, the appropriate pressure may be achieved by applying the amphiphilic molecules to the interface and achieving the appropriate pressure to form an ordered structure of the invention without compression.

The term "interface" includes interfaces at which amphiphilic molecules can be applied, such that an ordered structure is formed. Examples of interfaces include gas-liquid, gas-solid, liquid-gel, liquid-liquid, liquid-solid, etc. In a further embodiment, the interface is gas-aqueous. Examples of gases that may be used include those which do not adversely affect the formation of the ordered structures. Some examples include gases such as argon, nitrogen, air, carbon dioxide, oxygen, etc. Examples of liquids that may be used include aqueous solutions (e.g., buffer solutions, water, saline solutions, glycerin solutions), organic solvents, or any other liquids which do not adversely affect the amphiphilic molecules or ordered structure.

The amphiphilic molecule may be contacted with the interface by any method which allows for the formation of the ordered structures of the invention. Preferably, a population of amphiphilic molecules retain their native asymmetry or a uniform orientation. For protein amphiphilic molecules, the proteins may be contacted with the interface in the presence of a lipid membrane. For example, the proteins may be applied to the interface in the presence of a cellular membrane of a cell where the protein was expressed or overexpressed. Protein also may be applied to the interface in a liposome, proteoliposomes, a detergent solution, or by any method which allows for the formation of an ordered structure using the methods of the invention. In a further embodiment when the amphiphilic molecule is a protein (such as, for example, a membrane protein), the amphiphilic molecule is applied to the interface in a preparation which is essentially free of detergents (e.g., comprise less than about 0.1 or less percent detergent).

In a further embodiment, the method of the invention further comprises the formation of a planar membrane, comprised of at least the amphiphilic molecules, on the interface, prior to the formation of the ordered structure.

The term "planar membrane" includes monolayers, bilayers, and other membranes which are formed at the interface. The term "planar membrane" may be a monolayer, or bilayer, which when compressed, allows for the formation of ordered structures of populations of amphiphilic molecules. For example, amphiphilic molecules such as membrane proteins may be applied to the interface in the presence of lipids. The lipids and the proteins then form a planar membrane which then is compressed to form the protein ordered structures of the invention.

The invention pertains to methods of forming ordered structures of amphiphilic molecules, such as, but not limited to, integral membrane proteins, by planar membrane compression, as an alternative strategy to conventional two-dimensional and three-dimensional crystallization methods. This method allows one to influence and control a reorganization of membrane protein molecules within the monolayer to high packing densities necessary to induce nucleation and growth of crystals. Indeed, in some biological membranes ordered arrays have been observed simply from rearrangement of the protein within the membrane, either by removing the other membrane components or by induction with a specific agent. For example, crystallization of the cytochrome c oxidase was first observed accidentally during isolation and purification (Vanderkooi, G. et al. *Biochim. Biophys. Acta* 274, 38-48 (1972)). Crystallization upon reorganization has been particularly evident in biological membranes containing high levels of only a few different proteins at a high packing density.

Formation of two-dimensional ordered structures, e.g., two-dimensional crystallization, in planar membranes, in comparison with two-dimensional and three-dimensional crystallization from solution has some advantages. The methods of the invention can be adapted to use small microgram quantities of the amphiphilic molecule such as proteins.

For proteins and other molecules associated with membranes in their native state, the methods of the invention are advantageous because since the protein does not dissociate from the lipid, it is likely that the native asymmetry of the protein will be maintained in the planar membrane, i.e.; all proteins orienting in the same direction. Typically, proteins in two-dimensional crystals prepared from detergent solubilized membrane proteins resume a symmetrical orientation where alternating protein molecules face up and down.

In addition, in planar membranes, one can control and restrict the lateral mobility of the molecules of the planar membrane by varying their packing density. This may increase the chances of lattice formation in comparison with crystallization from an isotropic solution. In bilayers, possibilities for improving the crystallization conditions by varying experimental parameters are limited. In monolayer experiments, depending of the spreading conditions, the protein is exposed to no or negligible levels of detergent and is therefore more stable. However, exposing large proportions of a protein molecule to air or water during spreading may cause denaturation of the protein. Protein denaturation can be avoided by spreading the protein at a constant surface pressure, in order to ensure an optimized packing density. The presence of other membrane components, in native membranes may sometimes lead to disordered ordered structures. Reconstituting purified protein in the planar membrane can solve this problem. Alternatively, it can be minimized by using native membrane proteoliposome preparations including over-expressed protein.

This controlled ordering of amphiphilic molecules to a large flat domain, by compression, e.g., planar membrane compression, is suitable for preparation of ordered structures of a particular amphiphilic molecule for high-resolution atomic-scale structure analysis by electron diffraction and other electromagnetic radiation diffraction techniques known in the art. It was hypothesized that preparation of large, well-ordered and flat specimen, to a tolerance of better than 1° over 1 ($\mu m^2$ range, could decrease broadening of the diffraction spots and therefor provide better than 0.2 nm resolution (Glaeser, R. M. & Downing, K. H. *Ultramicroscopy,* 52, 478-486 (1993)).

The ability to form ordered ordered structures including, but not limited to nanostructures and two-dimensional and three-dimensional crystals, on a liquid in a fast and controlled fashion has many present and potential applications, which range from fields such as microelectronics, nonlinear optics to biotechnology, food, agriculture, cosmetics and home and personal care product development.

In a further embodiment, the invention pertains, at least in part, to a method for fabricating an ordered structure of a protein. The method includes expressing said protein in a cell, obtaining said protein from said cell, applying said protein to an interface, and compressing said protein on said interface to an appropriate pressure, such that an ordered structure of said protein is formed.

In a further embodiment, the protein is over expressed in the cell. In advantageous embodiment, the protein is a membrane protein and is found in a membrane of said cell. In a further embodiment, the protein is applied to said interface in the presence of membrane lipids, e.g., in a crude membrane preparation. Examples of proteins which may be used in the methods of the invention include, but are not limited to, membrane proteins, cellular receptors, orphan receptors, receptor tyrosine kinases, EPH receptors, ion channels, a cytokine receptors, multisubunit immune recognition receptors, chemokine receptors, growth factor receptors, or G-protein coupled receptors.

The term "over expressed" includes the enhancement in the amount of a particular protein of interest expressed by a host cell, by culturing in a suitable medium a host cell (e.g., a mammalian host cell such as a non-human mammalian cell) containing a recombinant expression vector, such that the protein is produced.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors comprise a nucleic acid containing the sequence of the desired protein in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, and the like. The expression vectors of the invention can be introduced into host cells to thereby produce proteins or peptides, including fusion proteins or peptides, encoded by nucleic acids encoding the desired protein to be expressed.

The recombinant expression vectors can be designed for expression of the proteins in prokaryotic or, advantageously, eukaryotic cells. For example, the proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of proteins. Examples of suitable inducible *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS 174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the protein can be carried out by standard DNA synthesis techniques.

In another embodiment, the HST-4 and/or the HST-5 expression vector is a yeast expression vector. Examples of vectors for expression in yeast *S. cerevisiae* include pYepSec1 (Baldari, et al, (1987) *Embo J.* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, the proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, the protein is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, *T. Molecular Cloning: A Laboratory Manual.* 2nd, ed., Cold Spring Harbor Laboratory, Cold Spring Harbor Laboratory Press, Cold Spring Harbor, N.Y., 1989.

A host cell can be any prokaryotic or eukaryotic cell. For example, the protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the protein or can be introduced on a separate vector. Cells stably transfected with the introduced nucleic acid can be identified by drug selection (e.g., cells that have incorporated the selectable marker gene will survive, while the other cells die).

In certain embodiment, the amphiphilic molecules of the invention may be applied to the interface in proteoliposomes which comprise more than one type of protein or lipid. Therefore, the resulting ordered structure may comprise one or more amphiphilic molecules (e.g., proteins, lipids, etc.).

For example, certain GPCRs involve a number of different membrane protein. Therefore, it is advantageous to reconstituting these proteins in proteoliposomes with more than one type of protein. Furthermore, it also may be advantageous to create ordered structures with more than one type of protein or lipid in cases where signal transmitted by the receptor is recognized and amplified by molecules other than the receptor itself, (such as, but not limited to, the G protein), and where the signal is subsequently transmitted to an effector molecule (which also may be a membrane protein). Ordered structures containing multi-protein and lipid systems may also be advantageous for other signal transduction pathways where the transduction of signal is initiated by hetero-dimer- or hetero-multimerization of different protein domains or protein species.

2. Two- and Three Dimensional Ordered Structures

The invention also pertains to two-dimensional ordered structures, comprised of a population of amphiphilic molecules. In a further embodiment, the two dimensional ordered structure comprises proteins, e.g., membrane proteins, cellular receptors, etc. In certain embodiments, the two dimensional ordered structures do not consist essentially of lipids. In a further embodiment, the two dimensional ordered structure of the invention is formed by planar membrane compression.

The term "planar membrane compression" is a method of forming ordered structures comprising contacting a population of amphiphilic molecules with an interface, compressing said population to an appropriate pressure laterally, such that a two-dimensional ordered structure is formed. In a further embodiment, the method includes formation of a planar membrane comprising the population of amphiphilic molecules prior to formation of the ordered structure.

The invention also includes three-dimensional ordered structures (e.g., "crystals") of amphiphilic molecules formed by the methods of the invention, e.g., contacting a population of amphiphilic molecules with an interface, compressing said population to an appropriate pressure (e.g., to or past the critical density), such that a three-dimensional ordered structure is formed.

In a further embodiment, the two- and three-dimensional ordered structures of the invention are suitable for structural determination of the amphiphilic molecule by diffraction techniques using electromagnetic radiation or neutrons.

In a further embodiment, the two- and three-dimensional ordered structures of the invention are mounted onto solid support.

The term "solid support" includes any support which allows for the ordered structure to perform its intended function. For example, for screening assays, the solid support may be selected such that it is suitable for manual or automated screening techniques. Examples of solid supports which may be used include, but are not limited to, glass, plastic, wood, and other materials suitable for use in the art. The solid support may further have a reactive, hydrophobic, hydrophilic coating. In other embodiments, the solid support may be a gel.

In certain embodiments, the solid support may be selected such that it is suitable for screening assays and other screening techniques. Example of screening assays include low, medium, high and ultra high-through put screening assays.

3. Structural Determination Using Ordered Structures

Biological instruments are important tools for numerous applications in pharmaceutical, biotechnology, agriculture, food and home, personal care and cosmetics industry. The invention pertains, at least in part, to novel technologies that can be used to study biological structure and function. For example, the methods and compositions of the invention may be used to develop nanotechnology for multiple applications such as for early stage drug discovery, target validation and lead optimization. The technology may be comprised of a nanofabrication system, interfaced with advanced optical analytical and micro diffraction techniques for fabrication of crystals and other ordered structures of amphiphilic molecules, such as membrane protein systems. For example, the invention pertains, at least in part, to protein chips (e.g., "NanoChip") for applications in screening assays, such as Structure-Activity Relationship (SAR)-based High Throughput Screening (HTS) systems. By combining technologies, the invention should streamline drug selection and lead identification processes for a wide range of membrane protein targets.

Low-resolution structure information (comparable to that obtained from an electron diffraction projection data at around 10-25 Å) can be obtained by using the methods and ordered structures of the invention. For example, fluorescence imaging of the two-dimensional ordered structures of amphiphilic molecules such as membrane proteins, formed at intermediate packing densities using planar membrane compression, provides information on the overall morphology of the protein molecules in their native habitat.

Imaging the shape or molecular outline of a membrane protein is important to probing biological recognition events. For example, cytokine-driven interactions appear to be the initial event in signal transduction for haemopoietin interferon receptors, receptor kinases, and the tumor necrosis factor (TNF)/nerve growth factor (NGF) receptors. In these systems, receptor multimerization allows information to pass from the extracellular domain to the cytoplasmic environment without a change in the conformation of the receptor. In some receptors such as those for epidermal growth factor (EGF) and platlet-derived growth figure (PDGF), dimerization of the receptor leads to activation of their intrinsic kinase activity. In yet another family, of receptors, e.g., the G-protein coupled receptors, seven membrane spanning receptors, it is believed that the binding of the agonist to the receptor initiates a change in the conformation of the receptor that is recognized by the associate G protein. In the signal transduction pathway, binding of molecular messengers (such as the human growth factors) to cell receptors (such as tyrosine kinases $TK_S$), initiates a series of complex events that generally starts with a change in conformation or dimerization of the protein. Signal transduction is involved in diverse cellular processes, including cell growth, reproduction, and migration. Any aberrations in these processes may result serious diseases such as cancer, diabetes, cardiovascular disease, and inflammation. In an embodiment, the invention pertains method for determining the shape of an amphiphilic molecule. The method includes contacting a population of the molecule with an interface, compressing said population to an appropriate pressure, such that an ordered structure is formed, and analyzing said ordered structure such that the shape of said amphiphilic molecule is determined.

The term "shape" includes both the three dimensional structure of a particular amphiphilic molecules in additional to the molecular outline of a particular molecule. The term "molecular outline" refers to the overall shape of the amphiphilic molecule in two dimensions such as that obtained from an electron density imaging map of a protein crystal at low resolution (5 Å or higher) and can identify alpha-helical regions as rods of electron density. The shape of the amphiphilic molecule can be used as a tool for rapid identification of a particular molecule or for determination of a change in conformation as well as hetero, homo, or other multimerization of particular species.

In one embodiment, the shape of said amphiphilic molecule is determined by using electromagnetic radiation diffraction. Examples of electromagnetic radiation which may be used includes, but is not limited to, light, electrons, x-rays, neutrons, or gamma rays. The shape of the amphiphilic molecule may also be determined by, for example, digital laser fluorescence video microscopy, x-ray crystallography, or electron crystallography. Advantageously, the shape of the amphiphilic molecule is determined to a resolution of about 5 Å or higher.

In a further embodiment, the methods of the invention can be used to detect the effect of test conditions on particular amphiphilic molecule by detecting shape changes of the molecule. In this method, the ordered structure is subjected to test conditions and the shape of the molecule is determined in the presence or absence of the conditions. In a further embodiment, the test conditions comprise contacting the amphiphilic molecule with a test compound.

In an embodiment, the invention pertains to methods for providing detailed structure information to near atomic resolution for amphiphilic molecules, such as membrane proteins. This is one of the most fascinating and challenging problems in structure-based (rational) drug design. If the protein is involved in either producing or preventing a disease state, information on its three-dimensional structure allows one to affect that disease state. This can be done, for example, by designing small molecules which interact with specific sites on the protein and alter its function or modulate its natural means of operation. The small molecules may inhibit, promote, antagonize, agonize, inverse agonize or otherwise alter the protein's activity.

The method includes obtaining an ordered structure comprising a population of amphiphilic molecules fabricated by the methods of the invention, e.g., planar membrane compression, and determine the structure of the amphiphilic molecules through electromagnetic radiation diffraction techniques. High-resolution structural information can be obtained from protein ordered structures formed using electromagnetic radiation diffraction techniques together with the methods of the invention described herein for the formation of ordered structures.

In a further embodiment, the invention includes a method for determining the structure of a protein. The method comprises the steps of expressing the protein in a cell, obtaining said protein from the cell (e.g., by harvesting the membrane), applying the protein to an interface (e.g., in a crude or purified preparation, preferably without the use of detergents), compressing the protein on the interface to an appropriate pressure, such that an ordered structure of said protein is formed, and analyzing the ordered structure (e.g., by electromagnetic radiation diffraction or other techniques) such that the structure of the protein is determined.

4. Screening Techniques Using Ordered Structures

In an embodiment, the invention pertains to a method for screening a ordered structures for binding or other interactions with a test compound. The method includes contacting the test compound with an ordered structure; and analyzing the results of the interaction of the test compound and the ordered structure, such that the test compound is screened. In a further embodiment, the ordered structure is comprised of protein, e.g., a membrane protein. In another further embodiment, the ordered structure is mounted on a solid support. Furthermore, the ordered structures may be incorporated into protein chips as described herein.

The term "screening" include both automated and manual techniques, and low, medium, high and ultra-high throughput screening techniques. The term includes all methods used by those in the art of screening including use of commercial plate readers, using imaging techniques described above as well as other binding assay including thermal transition analysis and detection systems using an analog or digital detection mechanism of the electromagnetic radiation. Such mechanisms by example include the eye(s) of the observer, CCD, photomultiplier tube, avalanche photodiode, etc. The test compounds may be screened for binding, agonist, antagonist, inhibitor, or activator activity. The term screening may refer to testing any number of test compounds or amphiphilic molecules desired. For example, the number of test compounds, amphiphilic molecules, proteins, etc. may range from one to greater than a million.

Examples of test compounds which may be used in the methods of the invention include small molecules, nucleic acids (e.g., RNA, DNA, etc.), carbohydrates, antibodies, and proteins. In certain embodiments, labeling the test compound may be advantageous. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Set U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223, 409), spores (Ladner USP '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222: 301-310); (Ladner supra.).

The term "small molecules" includes molecules such as peptides, peptidomimetics (e.g., peptoids), amino acids, amino acid analogs, polynucleotides, polynucleotide analogs, nucleosides, nucleoside analogs, nucleotides, nucleotide analogs, organic (including, e.g., heteroorganic and organometallic compounds) and inorganic compounds including metals which may bind to the protein or amphiphilic molecule. The term "small molecule" includes compounds which have a molecular weight of about, for example, 10,000 grams per mole or less, 5,000 grams per mole or less, 2,000 grams per mole or less, or 1,000 g/mol grams per mole or less. In a further embodiment, the small molecule is an organic compound. Organic compounds comprise one or more carbon atoms. In another embodiment, the compound is an inorganic compound. Inorganic compounds include compounds which do not comprise a carbon atom.

The invention provides a method (also referred to herein as a "screening assay") for identifying modulators, i.e., test compounds or agents (e.g., peptides, peptidomimetics, small molecules or other drugs) which bind to the amphiphilic molecules of the ordered structures of the invention which have a stimulatory or inhibitory effect on, for example, the amphiphilic molecule's activity.

In one embodiment, the invention provides assays for screening candidate or test compounds which are substrates of an amphiphilic molecule. In another embodiment, the invention provides assays for screening candidate or test compounds which bind to or modulate the activity of an amphiphilic molecule.

The ability of the test compound to modulate the binding of an amphiphilic molecule to a substrate can be determined. Determining the ability of the test compound to modulate the binding of an amphiphilic molecule to a substrate can be accomplished, for example, by coupling the amphiphilic molecule's substrate with a radioisotope or enzymatic label such that binding of the amphiphilic molecule's substrate to the amphiphilic molecule can be determined by detecting the labeled amphiphilic molecule's substrate in a complex. Alternatively, the amphiphilic molecule could be coupled with a radioisotope or enzymatic label to monitor the ability of a test compound to modulate the amphiphilic molecule's binding to a substrate in a complex. Determining the ability of the test compound to bind an amphiphilic molecule can be accomplished, for example, by coupling the compound with a radioisotope or enzymatic label such that binding of the compound to the amphiphilic molecule can be determined by detecting the labeled amphiphilic molecule compound in a complex. For example, compounds (e.g., the amphiphilic molecule's substrates) can be labeled with $^{125}$I, $^{35}$S $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

In an embodiment, an assay of the present invention comprises contacting an amphiphilic molecule with a test compound, such that the ability of the test compound to bind to the amphiphilic molecule is determined. Binding of the test compound to the amphiphilic molecule can be determined either directly or indirectly. In an embodiment, the assay includes contacting the amphiphilic molecule with a known compound which binds the amphiphilic molecule to form an assay mixture, contacting the assay mixture with a test compound, and determining the ability of the test compound to interact with an amphiphilic molecule, wherein determining the ability of the test compound to interact with an amphiphilic molecule comprises determining the ability of the test compound to preferentially bind to an amphiphilic molecule as compared to the known compound.

In another embodiment, a test compound is contacted with an ordered structure and the ability of the test compound to modulate (e.g., stimulate or inhibit) the activity of the amphiphilic molecule of the ordered structure is determined. Determining the ability of the test compound to modulate the activity of an amphiphilic molecule can be accomplished, for example, by determining the ability of the amphiphilic molecule to bind to a target molecule. Determining the ability of the amphiphilic molecule to bind to a target molecule can be accomplished using a technology such as the methods of the invention.

In yet another embodiment, the assay involves contacting an amphiphilic molecule with a known compound which binds the amphiphilic molecule to form an assay mixture, contacting the assay mixture with a test compound, and determining the ability of the test compound to interact with the amphiphilic molecule, wherein determining the ability of the test compound to interact with the amphiphilic molecule comprises determining the ability of the amphiphilic molecule to preferentially bind to or modulate the activity of the known compound.

The analysis of the interaction of the test compound and the ordered structure may comprise analyzing the shape changes of the protein. Shape changes include conformational changes (e.g., folding, unfolding), multimerization (e.g., dimerization, trimerization, etc.), fragmentation, and other changes which can be detected using the methods of the invention.

For example, in an embodiment, the interaction between the protein and a test compound can be monitored using high-performance CCD or other digital or analog imaging techniques and/or by capturing the photon using the eyes, a CCD, a photodiode, or a photomultiplier tube. Sonveaux et al. reported a change in the tertiary structure of reconstituted P-gp both in the presence and in the absence of MgATP, and MgATP-verapamil (*J. Biol. Chem.* 271, 24617-24 (1996)). In the methods of the invention, the change in the shape of the P-gp would be monitored, for example, by fluorescence imaging of the domains, using a fluorescent analog of verapamil (Molecular Probes) in the presence and absence of MgATP.

In a further embodiment, the interaction of the amphiphilic molecule, such as a protein (e.g., a receptor) with the test compound can be monitored using thermal microanalysis, whereby binding of the test compound to the receptor is monitored through depicting a change in the thermal transition of the receptor in the presence and absence of the test compound using microcalorimetry.

The methods of the invention take advantage of the quantitative imaging capability of advanced imaging as well as photon counting techniques such as high-performance CCDs, to demonstrate simple binding assays to depict high-affinity binding of a ligand such as verapamil to P-gp. A variety of different illumination techniques may be used to measure equilibrium binding of a test compound to the protein, for example, two such techniques include (1) incident light (epi-) illumination may be used to monitor interactions of high binding affinity ligands. Total Internal Reflection Fluorescence (TIRF) using a block preferably with cylindrical symmetry may be integrated with the imaging system to probe equilibrium binding affinity of low-affinity binding ligands directly at equilibrium and without perturbing the equilibrium (Mojtabai, F., *Ph.D. Thesis* pp. 1-129 (University of Basel, Switzerland, 1985). Superior characteristics of TIRF vs. incident-light illumination have been discussed in detail elsewhere. Briefly these include a low depth of penetration of light to allow optical sectioning to 20 nm in the z direction. This low depth of penetration reduces background illumination from out of focus planes in the solution. This significantly enhances the sensitivity of binding assays. These fluorescence illumination by epi-fluorescence or TIRF may be combined with Fluorescence Recovery After Photobleaching or Polarized Fluorescence Recovery After Photobleaching to measure binding kinetics and degree of aggregation.

The methods of the invention also may be used for identifying particular proteins of interest in tissue samples (e.g., blood, muscle, fat, hair, cells, etc.), by obtaining a sample of a cell, applying the sample to the interface, compressing the sample on said interface to an appropriate pressure, such that an ordered structure is formed; and identifying the protein of interest in the ordered structure. Preferably the sample of a cell is a membrane preparation, e.g., a crude membrane preparation. In one further embodiment, the identification method involves contacting the ordered structure of the invention with an agent which binds to the ampiphilic molecule of interest. Agents which bind to proteins and can be detected are known in the art. Examples of agents which can bind to proteins include antibodies.

Furthermore, the assay methods of the invention may further comprise the use of ordered structures which are comprised of more than one type of amphiphilic molecule in the ordered structure. These ordered structures can be synthesized by applying multicomponent proteoliposomes to an interface and compressing it to an appropriate pressure to yield an ordered structure of the invention.

In an embodiment, these multicomponent proteoliposomes may include a mixture of amphiphilic materials such as, but not limited to, phospholipids, cholesterol and the membrane protein beta amyloid precursor protein (APP). The resulting ordered structures of membrane preparations may be used to develop an assay to determine how lowering cholesterol might inhibit clipping of the APP by certain enzymes to prevent formation of the neurotoxic peptide beta-amyloid and to subsequently inhibit the formation of plaques in the Alzheimer's disease. In a recent article, new research suggests that cholesterol-lowering treatments inhibit formation of beta-amyloid by shifting the balance of activities of enzymes that clip the APP (such as the beta-, and gamma-secretase) to produce the neutrotoxin, to favor those enzymes (such as the alpha-secretase) that prevent the production of the neurotoxic peptide (*Science* Vol. 294, Pages 508-509). It has thus been deduced that beta-, and gamma-secretase may have greater access to clip APP in cholesterol rich cell membrane rafts than in phospholipid rich areas of the cell membrane. Such analysis may lead to development of new diagnostics and therapeutic systems that can be used to detect and cure the Alzheimer's disease.

5. Protein Chips and Other Ordered Structure Products

As DNA-based biochip technology continues to find applications in DNA analysis, the protein chips (e.g., protein "Nanochips") of the present invention may also be used in numerous applications. In one embodiment, the invention pertains, at least in part to a protein chip, which includes a solid support and at least one ordered structure of a population of amphiphilic molecules. The ordered structures of the protein chip may be either two or three dimensional. The protein chip may also further comprise additional ordered structures of the same or different amphiphilic molecules. The protein chip may comprise ordered structures of any number of amphiphilic molecules, preferably with each different amphiphilic molecule contained in discrete wells. The number of ordered structures of amphiphilic molecules may range from one to tens of thousands or more. In other embodiments, ordered structures of the same amphiphilic molecule is present in each of the wells of the protein chip. In certain embodiments, the amphiphilic molecules of the protein chip are proteins and, in yet a further embodiment, may be membrane proteins. Preferably, the protein chip is suitable for screening methods, e.g., automated screening techniques such as low, medium, high and ultra-high through put screening techniques.

The methods of the invention will be used to create protein chips (e.g., "NanoChip"). The basic design of the protein chip will have flexibility to be suitable for use in screening assays, such as, but not limited to, High Through-put Screening (HTS) systems. Alternatively, the invention also pertains, at least in part, to a stand-alone SAR-based Ultra High-Throughput Screening (UHTS) system, by integrating the protein chip (e.g., "NanoChip") with highly sensitive optical detection systems and advanced microrobotics technologies. The protein chips of the invention are expected to meet the market needs for automation, higher sensitivity, accuracy and precision as well as increased sample throughput and decreased unit cost. Other applications of the protein ("NanoChip") are in developing analytical devices to probe molecular recognition events, or alternatively, it can be incorporated into diagnostic imaging devices.

The protein chip can be used for a wide-range of applications in different areas; such as receptor-ligand interactions, competitive binding analysis, monitoring ligand-induced conformational changes, protein structure analysis, immunoassays, enzyme-substrate interactions, protein quantification, trace protein detection, protein-DNA interactions, as well as monitoring gene expression. Other areas include probing the signal transduction events, and developing diagnostics imaging devices, for example to assay Multidrug Resistance.

Preferably, the protein chip of the invention comprises a plurality of ordered structures in discrete wells. The number of wells can be any number which allow the protein chip to perform its intended function. For example, a protein chip may comprise numerous wells with the same protein in ordered structures in each discrete well, or different proteins in ordered structures in each discrete well. In yet another embodiment, the invention also includes compatible components for future use in commercial fluorimetric microplate readers or imagers.

Figure 1B:
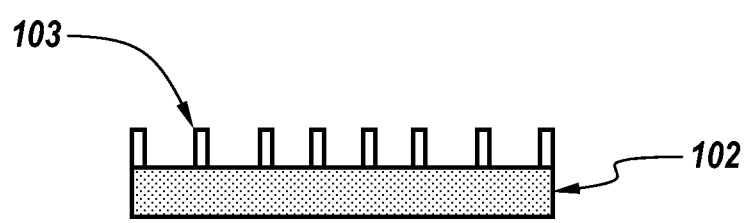

In a further embodiment, the protein chip comprises discrete ordered structures in a multiwell array (e.g., high density multiwell array), on a solid substrate, preferably formed of a transparent, rigid substance, such as fused silica. The two-dimensional or three-dimensional ordered structures of proteins may be extended from a single-well (for example, the glass bottom of a trough as described in U.S. Pat. No. 5,044,308) to a multi-well array. A schematic drawing of a protein chip of the invention is shown in FIGS. 1*a* and 1*b*. FIG. 1*a* is a top view of the plate 100 of the trough 10 including a plurality of micro-wells 101 for fabricating an array of ordered structures of membrane proteins. FIG. 1*b* is a cross-sectional view of the plate 100 illustrated in FIG. 1*a*. As shown, the arrays are formed on a glass substrate 102 or a substrate formed of another suitable material. The microwells are formed by fabricating raised polymer walls 103 on the substrate. Preferably, the polymeric compound is a hydrophobic inert material, such as a fluoroelastomeric material, e.g., Teflon (DuPont), and are between about ten and about twenty microns thick. Briefly, a negative mask is fabricated using a thin, flat piece of metal or plastic, to denote the raised rims of each well 101. The mask is placed on the glass substrate 102 of the trough. A thin film, preferably between about ten and about twenty microns, of liquid Teflon (DuPont) is sprayed or deposited on the glass substrate 102 in order to cover the unmasked regions. To ensure better adhesion of Teflon to glass, the unmasked regions may be pre-etched prior to the deposition process. Different sizes and shapes of micro-wells can be fabricated on the glass substrate by using different mask geometry. The solvent will be allowed to evaporate by application of heat or drying under a stream of nitrogen to prevent contamination of the substrate with impurities.

After formation of the wells, the glass substrate is mounted at the bottom of the trough. Ordered structures are fabricated as described earlier. The ordered structures are transferred to the protein chip, by a horizontal deposition, namely by lowering the depth of water in the trough until the height of the film of water reaches the height of the raised walls of the trough. Further lowering of the depth of water will cause a separation between the contents of each well as the film of water breaks at the raised heights surrounding the well. Alternatively, the ordered structures may be transferred to a different solid support (e.g., another chip), at a gas/solid, liquid/solid, or solid/solid interface. The micro structure may be cryo-preserved for electron microscopy and diffraction analysis or for purposes of preservation until future use. The transfer process may be made manually or remotely by using a robotic arm. The solid support may constitute a chemically inert, hydrophobic or hydrophilic material coated or uncoated with functionally active or inactive compounds. Such materials include, for example, glass, quartz, metals, metal oxides, silicon oxide, teflon, plastics, and mica. Each material may be coated with a layer of other materials such as graphite or silica oxide or gels including functionally active compounds to capture the ordered structures. The contents of each well can then be analyzed independent from other surrounding wells. The fidelity of the transfer of the ordered structures to the chip will be assessed, by fluorescence microscopic monitoring of the shape of the protein ordered structures. Alternatively, one can measure binding of a test compound to the protein in a quantitative or qualitative SAR-based HTS screening mechanism using an analog or digital detection technique such as a CCD, photomultiplier, or avalanche photodiode. Future commercial production costs should be low due to the availability of robust microfabrication procedures such as aqueous-based etch procedures, and photoresists for precise patterning the wells (Burns, M. A., et al. *Science* 282, 484-487 (1998)).

The protein-chip, (e.g., "NanoChip"), together with such advanced surface-selective illumination techniques constitutes the basic components of an integrated turn-key high throughput screening system. Alternatively, the protein chip may be used in existing commercial microplate readers or other imaging devices.

Applications of protein chips, include, for example, an integrated SAR-based HTS or a functional group imaging system in combination with a nanotip AFM or by using Surface Plasmon Polaritons. Chemically modified nanotube tips, that are now available for atomic force microscopy (AFM) of biological specimen, can be used for functional group imaging of the ordered structures (Wong, S. S. et al. *Nature* 394, 52-55 (1998)). In addition, the nanotip AFM can be used in combination with fluorescence imaging of the ordered structures to provide a topographic three-dimensional view of the amphiphilic molecule's molecular outline.

The ordered structures of amphiphilic molecules can be attached or otherwise associated with a solid support to facilitate screening assays. Binding of a test compound to an amphiphilic molecule of an ordered structure, or interaction of an amphiphilic molecule of an ordered structure with a target molecule in the presence and absence of a test compound, can be accomplished in any vessel suitable for containing the reactants. Examples of such vessels include micro titer plates, such as the protein chips of the invention. For example, the protein chips may be combined with the test compound, and the mixture incubated under conditions conducive to complex formation (e.g., at physiological conditions for salt and pH). Following incubation, the protein chip wells are washed to remove any unbound components, complex determined either directly or indirectly, for example, as described below.

6. Apparatus and Instrumentation for Formation and Analysis of Ordered Structures Special instrumentation may be useful if this process is to be used in diverse disciplines for a wide range of applications. Specifically, fabrication of ordered structures by compression a planar membrane beyond a critical density point (over-compression) barriers that are resistant to film leakage at high surface pressures may be advantageous. Advantageously, the instrument also should provide for: (i) controlled fabrication of uniform micro- and nanostructures, (ii) monitoring the formation of the structures by real-time fluorescence imaging, and (iii) transferring the micro- and nanostructures to a solid support for atomic scale measurements.

In an embodiment, the invention pertains to a system for controlled fabrication of ordered structures of amphiphilic materials, e.g., membrane proteins. The system may be integrated with advanced surface selective fluorescence and non-fluorescence imaging systems, as well as a robotic mechanism to transfer the fabricated ordered structures to a solid support for preparation of specimen and a device to subsequently flash freeze the proteins in the ordered structures at cryogenic temperatures.

The illustrative embodiment of the invention provides an integrated trough system for forming and analyzing an ordered structure on a subphase in an efficient and controlled manner. According to the illustrative embodiment, the system of the present invention includes a trough for the forming an ordered structure by compression of a population of amphiphilic molecules. The trough includes a barrier for compressing the population that is resistant to leakage at high surface pressures. A suitable trough is described, for example, in U.S. Pat. No. 5,044,308, the contents of which are herein incorporated by reference. The integrated trough system includes an image acquisition and processing system integrated with the trough for acquiring, processing, storing and printing images of the ordered structure formed by the trough. The integrated system further includes a temperature regulated housing for maintaining a precise temperature during formation of the ordered structure, and an automated ordered structure transfer system for transferring an ordered structure formed in the trough to a cryochamber. The integrated trough system of the illustrative embodiment allows for controlled fabrication of uniform ordered structures, monitoring of the formation of the ordered structures in real-time and transferring of the ordered structures to a solid support for atomic scale measurements.

Briefly, the trough used in the illustrative embodiment of the invention and described in U.S. Pat. No. 5,044,308 is used to fabricate ordered structures at air-aqueous interfaces via planar member compression and comprises a frame having top and bottom separable frame portions. A plate is disposed within the frame for holding a subphase. The plate is preferably formed of a transparent rigid substance, such as fused silica to allow imaging through the plate of a structure formed thereon. A sealing element of chemically inert material is positioned between the top of the plate and the top frame portion and preferably comprises a perfluoroelastomeric material that is conformable to the top of the plate and to the top frame portion to prevent subphase leakage from the trough. A movable barrier is provided for laterally compressing a population of amphipilic molecules deposited on the subphase to form an ordered structure. An additional sealing element of chemically inert material may be spaced adjacent to the above-mentioned sealing element, and also positioned between the top of the plate and the top frame portion for cooperating with the above-mentioned sealing element to prevent the subphase from reaching the frame. One skilled in the art will recognize that the present invention is not limited to the trough described in U.S. Pat. No. 5,044,308, and that any suitable structure for forming an ordered structure by compression may be utilized.

An advantage of the trough described in the '308 patent is that the configuration of the trough allows for a lower depth of water in the plate, typically less than 0.5 mm. The reduced water depth reduces conventional flow transferred from the aqueous subphase to the ordered structure, thereby permitting direct fluorescence microscopic observation of distinct features in the ordered structure without requiring the use of flow retardation devices commonly used in other microscope troughs, which limit the observation area and perturbs the ordered structure.

Figure 2:
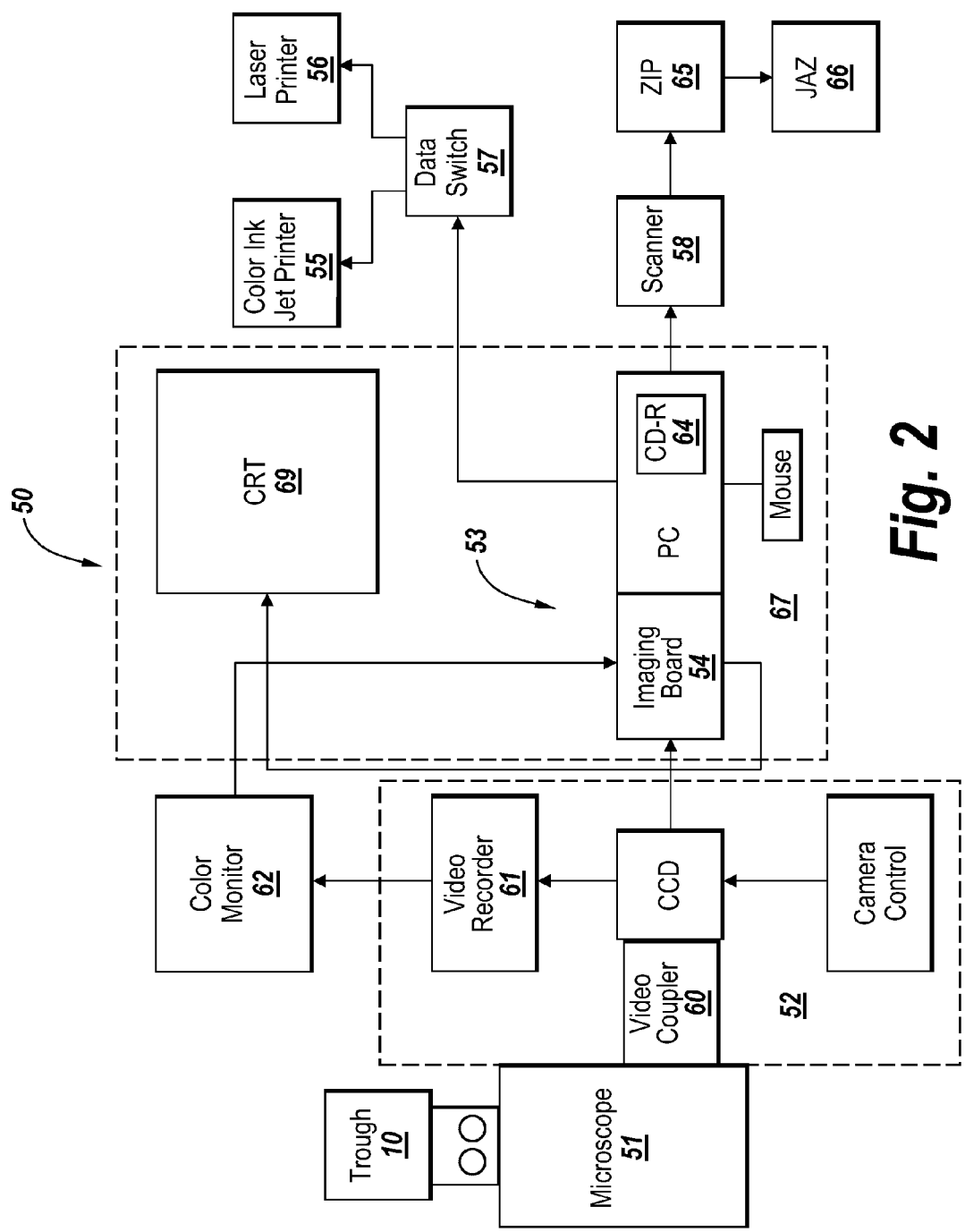
FIG. 2 is a block diagram of the integrated trough system including and image acquisition and processing system for viewing and analyzing a sample formed in the trough according to the illustrative embodiment.

According to the illustrative embodiment, shown in FIG. 2, the trough 10 is integrated with an image acquisition and processing system 50 to allow for in-situ characterization of the structure formation throughout the fabrication process. In the illustrative embodiment, the imaging and image processing system is a real-time digital laser-fluorescence video microscopy system including an inverted fluourescence microscope 51, such as an Olympus IMT-2 equipped with epi-illumination optics for viewing the trough 10. The microscope 51 is connected to a video camera 52 for generating, storing and displaying analog video signals representative of the ordered structure viewed by the microscope. The video camera is connected to a monitor 62 for displaying the video image and processor 53, including an imaging board 54 for storing still frame digital images of the ordered structure formed in the trough. The imaging board is connected to a second monitor 69 for displaying the digital images of the ordered structure. The illustrative image acquisition and processing system further includes color ink jet printer 55 for printing color images and a laser printer 56 for printing black and white images. A data switch 57 directs a data signal representative of an image of the ordered structure to a selected printer. The system further includes a scanner system 58 for scanning transparencies and negatives and storage devices for storing the digital images. One skilled in the art will recognize that the invention is not limited to the illustrative image acquisition and processing system, and that any suitable arrangement for acquiring, storing, viewing, processing and/or printing images of the structure formation may be utilized.

The illustrative trough 10 is mounted on the stage of the inverted fluorescence microscope 51 to allow visualization of an ordered structure formed in the trough. A light source, such as a laser or a lamp, excites selected fluorescent probes within the ordered structure. According to the illustrative embodiment, an air-cooled argon laser is used to excite fluorescence emission with either a 488 or 514 nanometer line. The microscope of the illustrative embodiment is equipped with two different sets of filters for emission of FITC, as well as rhodamine-type fluorescence. The fluorescein filters of the illustrative embodiment include a 505-nm dichroic long pass filter and a 515-nm long pass emitter, from Chroma Technology Corporation. The rhodamine filters may comprise a 565 nm dichroic long pass filter and a 580-nm long pass emitter. After the light source excites the ordered structure in the trough 10, the emitted fluorescence from the ordered structure is observed through the microscope objective. In order to observe the ordered structure, a small amount, between about 1-2 mole %, of a fluorescent amphiphilic dye is mixed with the population of amphiphilic molecules. A high power, high numerical aperture objective with high collection efficiency can be utilized, due to the low depth of water in the trough. The illustrative configuration allows imaging by optical sectioning throughout the shallow aqueous subphase, which is accomplished by zooming the objective at different heights through the transparent plate at the bottom of the trough. In this manner, the integrated system permits tracking of the formation of micro structures throughout the entire working volume of the trough, e.g. at the air-water interface, throughout the shallow aqueous subphase, as well as the liquid solid interface at the bottom of the trough.

According to the illustrative embodiment, the video camera 52 is a Sony DXC-9000 color video camera attached to the microscope 51 via a video coupler 60, though one skilled in the art will recognize that any suitable electronic device for recording images of an object may be utilized. The imaging device of the video camera of the illustrative embodiment incorporates three ½ inch progressive scan CCD chips. The dynamic resolution of the images is 700× 480 TV lines. A video recorder 61, such as a Sony Videocassette Recorder model SVO09500MD, records an analog video signal representative of an image captured by the microscope in real-time. A color monitor 62, such as a 13-inch PVM-14N2U Sony color video monitor with 500 TV line resolution, in communication with the video camera 52, displays the video signal generated by the video camera.

According to the illustrative embodiment the imaging board 54 is a FlashPoint-128™ high performance high resolution video capture board from Integral Technologies with a 4 Mb MDRAM and SuperVGA Window application. The processor 53 containing the board 54 comprises a Pentium II 300 Mhz in a model G6-300 personal computer 67 from Gateway having a 4 GB SCSI hard drive, 128 MB RAM running under a Window operating system. The analog outputs of the imaging board 54 are connected to the appropriate inputs of the computer monitor 69, illustrated as a 19-inch EV900 color CRT from Gateway with a 1600× 1200 maximum resolution and 0.26 pitch. One skilled in the art will recognize that any suitable imaging board and processor may be utilized to process and store still frame digital images of the ordered structure formed in the trough, in accordance with the teachings of the invention.

According to the illustrative embodiment, images of the ordered structure are acquired and processed using ImagePro Plus 3.0 software for Windows 95 from Media Cybernetic, and dynamic time-lapse or real-time representations are made using the ImagePro Plus Sequencer function, allowing a user to view a sequence of stored image files at a controlled speed. A storage device, such as a 650 Mb Hitachi CD-R 64, an Iomega 1Gb Jaz 65, a 100 Mb Zip drive 66 or any other suitable storage device may be utilized to archive the digital data. Digital images can be processed for color contrast and brightness enhancement using the Adobe PhotoShop 4.0 or any other suitable processing software. According to the illustrative embodiment, the color printer 55 comprises an Epson Stylus Color 800 Ink Jet output device with up to 1440×720 dpi resolution using Epson Photo Quality Ink Jet paper at 720 dpi. The black and white laser printer 56 of the illustrative embodiment comprises an HP LaserJet 6P/6MP printer with 600 dpi resolution. The scanner 58 of the illustrative embodiment comprises a Microtek ScanMaker III 36-bit flatbed scanner with 600× 1200 dpi optical resolution (96,000 dpi interpolated). The scanner 58 includes a Transparent Media Adapter to allow scanning transparencies and negatives. One skilled in the art will recognize that the invention is not limited to the illustrative embodiment and that variations may be made without departing from the scope of the invention. For example, the image acquisition and processing system is not limited to the described printers, scanner, storage devices and software and any suitable product may be utilized.

Figure 3A:
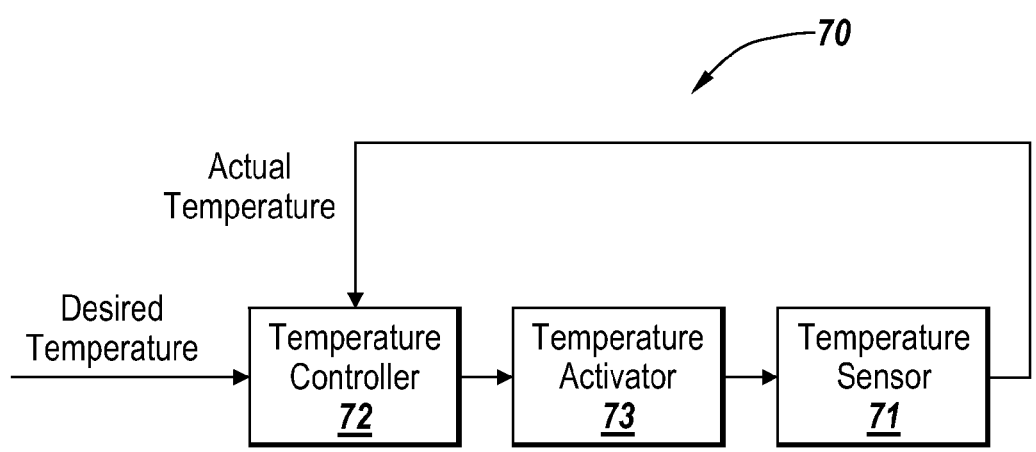
FIG. 3a is a block diagram of a feedback control system for controlling the temperature of the trough according to the illustrative embodiment.
Figure 3B:
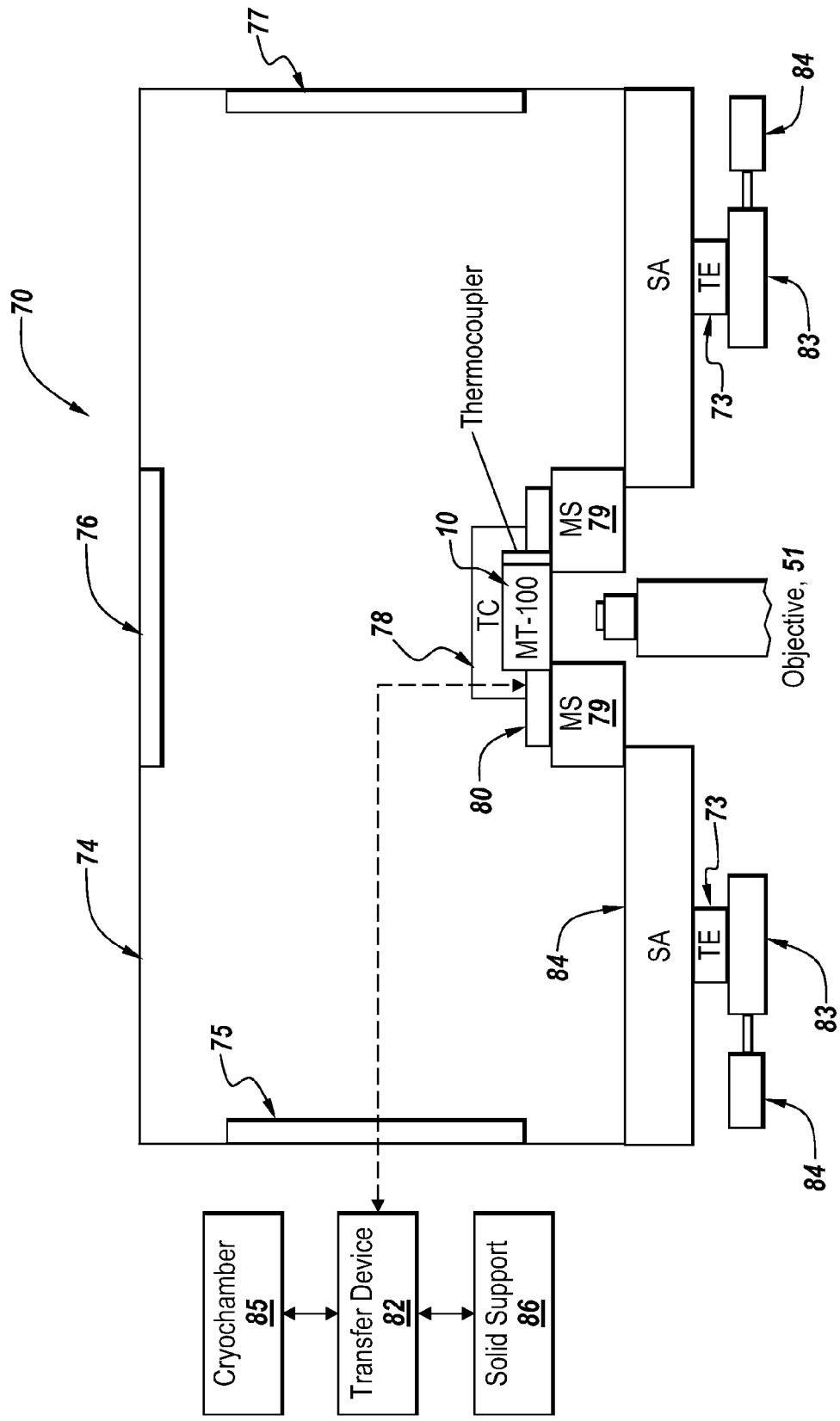
FIG. 3b is a schematic diagram of the temperature regulated housing system for controlling the temperature of a subphase in the trough of the illustrated embodiment.

According to one embodiment, shown in FIGS. 3a and 3b, the trough 10 is utilized with a temperature regulated housing system 70 for accurately controlling the operating temperature within the trough environment during formation of the ordered structure. The illustrative temperature control system 70 provides precise temperature regulation within a −10 to +40° Celsius range to within +−−0.1° Celsius of a selected reference temperature. The illustrative temperature regulated housing comprises a proportional-integral feedback control system, illustrated in the block diagram of FIG. 2a. The control system includes a temperature sensor 71 for measuring the temperature of the subphase in the trough 10 and a temperature actuator 73 for adjusting the temperature within the trough 10. The temperature control system further comprises a controller 72 for controlling the actuator 73 in response to the actual temperature measured by the sensor 71. The controller 72 inputs are the actual temperature signal measured by the temperature sensor and a selected reference temperature signal, set by a user. The controller 72 compares the actual temperature to a desired temperature and triggers the actuator 72 to adjust the actual temperature by a selected amount to equal the desired temperature.

As shown in FIG. 3b, the temperature control system 70 controls the temperature within an enclosed volume defined by a housing 74 enclosing the trough 10. According to the illustrative embodiment, the housing 74 is formed of 0.5 mm thick plexiglass, though one skilled in the art will recognize that alternate materials may be utilized. The illustrative housing 74 encloses a volume of less than about 51 liters around the trough 10. The housing includes a plurality of sealable openings 75, 76, 77 to facilitate access to the trough. The openings 75, 76, 77 are sealed from the outside by sliding doors formed of plexiglass. An inner trough cover 78, also preferably formed of plexiglass, directly covers the trough 10, which is mounted onto the microscope stage 79 via a microscope trough adapter 80. The temperature controlled housing system 70 further includes a microscope stage adapter 81 for mounting the housing 74 to the microscope stage 79.

The integrated system further includes an automated ordered structure transfer device 82, comprising a robotic arm, for transferring an ordered structure formed in the trough 10 according to the teachings of the present invention to a solid support 86 for further atomic scale examination. The solid support may comprise a small solid support, such as an electron microscope grid or large solid support, such as a microscope cover glass or an oxidized silicon support. The ordered structure transfer device 82 accesses the trough 10 through the one of the openings 75, 76, 77 in the housing 74. A number of analytical techniques can be employed to the supported ordered structure in order to characterize its structure to subnanometer resolution. These techniques include high-resolution electron microscopy, electron-diffraction, synchrotron micro-focus x-ray diffraction, as well as scanning probe microscopies, such as atomic force microscopy (AFM) or near-field scanning optical microscopy (NSOM). Molecular recognition events and low resolution structural analysis of the protein can be further studied at either an air-aqueous interface or at a solid support using a number of advanced surface-selective techniques, including Total Internal Reflection Fluorescence (TIRF) and Fluorescence Recovery After Photobleaching (FRAP), with polarized or non-polarized illumination, Surface Plasmon Polaritons (SPP), and Scanning Probe Microscopies, such as AFM. The illustrated system further comprises a cryochamber 85 for preserving a specimen formed in the trough at cryogenic temperatures in a frozen hydrated state for further analysis.

The temperature actuator 73 of the illustrative embodiment comprises a pair of thermoelectric cooling devices (TEC) mounted diagonally below the microscope stage adapter 81. The thermoelectric cooling devices 73 produce a temperature differential to increase or decrease the temperature in the trough 10. A thermoelectric cooling device is a special type of semiconductor that functions as a heat pump. By applying a low-voltage, high-current, DC power source, heat will be moved in the direction of the current. The heat is pumped from one side of the thermoelectric cooling device to the other, so that one face will be cold while the opposite face will be heated, and the effect is reversible. One skilled in the art will recognize that any suitable device for heating or cooling the trough subphase and/or trough environment may be utilized. The illustrative temperature sensor 71 for measuring the temperature of the subphase in the trough comprises a K-type thermocouple model KMTSS-0100G-6, with a probe diameter of 0.010" and SMP-K-M connector, though one skilled in the art will recognize that any suitable temperature sensor may be utilized. The thermoelectric cooling device applies the temperature differential to the trough via an aluminum plate in the bottom of the housing 74, which cools the aqueous subphase in the trough by convection of heat. According to the illustrative embodiment, the maximum heat pump of the thermoelectric cooling devices 73 is 127 watts, operating at 14 amps, capable of producing a "no load" temperature differential of approximately 67° C. A pair of liquid heat exchangers 83 located below the thermoelectric cooling devices form heat sinks for absorbing the heat produced on the hot side of the thermoelectric modules during a cooling cycle. The liquid heat exchangers 83 are cooled by water at about 0° C. A peristaltic pump 84 is provided to move water through liquid-sealed pipes in the heat exchanger at a rate of about 10 ml/s. One skilled in the art will recognize that any suitable device for providing a heat sink may be utilized.

Figure 4A:
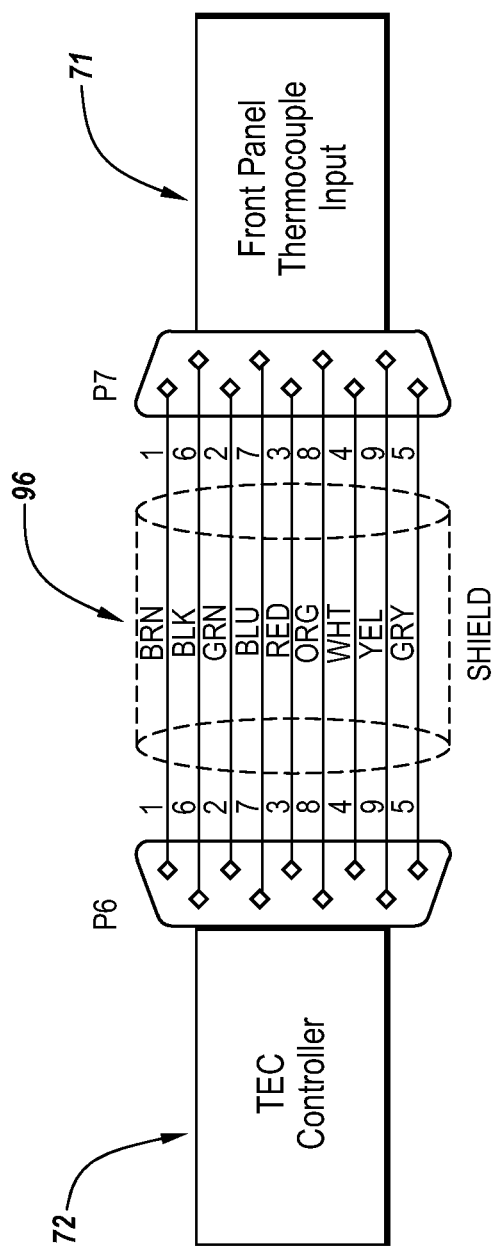
FIGS. 4a and 4b are schematic diagrams of the electronics in the temperature-regulated housing system of FIGS. 3a and 3b.
Figure 4B:
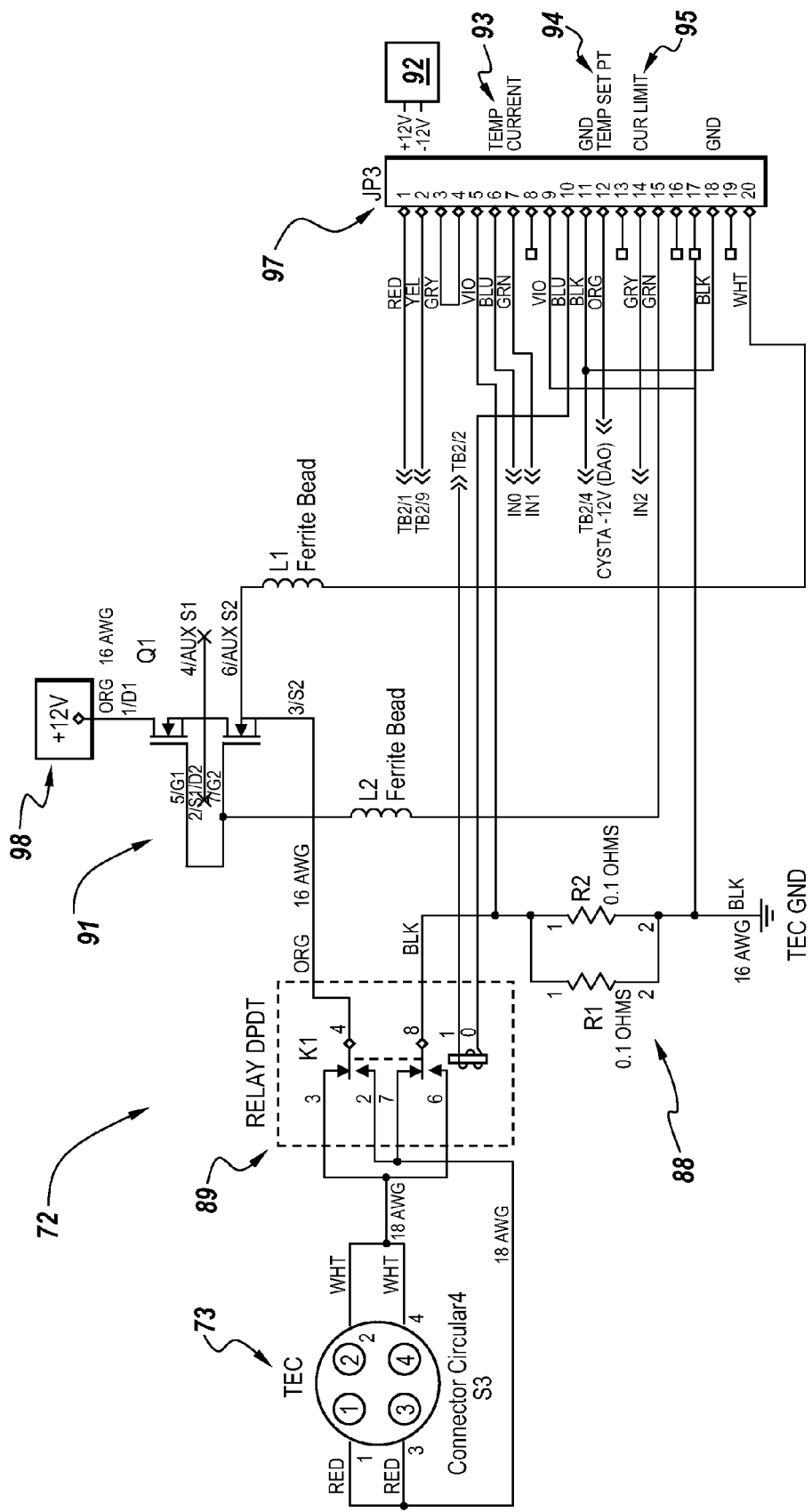

FIGS. 4a and 4b are schematic diagrams of the electronic temperature control design system for controlling the temperature of the subphase according to the illustrative embodiment. The output of the temperature sensor 71, corresponding to the temperature in the subphase, is integrated via a closed loop circuit to a proportional-integral (PI) controller board 72 designed to be used with a thermoelectric cooling device or other suitable cooling device or heat pump. As shown in FIG. 4a, a conductor-shielded cable 96 provides an electrical connection between the temperature sensor 71 and the controller board 72. The controller board 72, shown in detail in FIG. 4b, controls the input to the thermoelectric cooling device 73, which accordingly determines the temperature in the trough.

According to the illustrative embodiment, the controller board 72 is a Series P-1 Thermoelectric Cooler controller board from Alpha Omega Instruments Corp. The controller 72 features a metal oxide semiconductor field-effect transistor 91 (MOSFET) or other suitable power amplifier, together with proportional and integral (PI) temperature control. The illustrative controller board 72 is powered by a DC power source 92. The illustrative controller board comprises an input/output system, such as a twenty-pin Molex connector 97, for attaching the temperature control system to a temperature control interface board. The connector 97 includes input control lines for the connecting the power supply 92 to the connector 97, the current temperature input 93, transmitted from the thermocouple 71, a reference temperature set point 94 for setting the desired temperature of the subphase and a maximum current set point 95. According to the illustrative embodiment, the temperature set point and maximum set point are adjusted by the user using single-turn adjustment potentiometers. As illustrated, the MOFSET 91 is located between the TEC 73 and a TEC power supply 98. The controller board 72 further includes a current sense resistor 88, illustrated as two 0.1 ohm resistors in parallel, connected to ground and a double-pole, double-throw (DPDT) relay 89. Relays are electromagnetic switches that can turn a large amount of current on or off by using a relatively small amount of current. The relay 89 allows the controller 72 to operate in unipolar (i.e. providing heating or cooling) or bipolar (i.e. providing heating and cooling) mode. One skilled in the art will recognize that any suitable switch for allowing bipolar operation may be utilized according to the teachings of the invention.

To control the temperature in the trough, the temperature sensor 71 measures the current temperature in the trough and transmits a current temperature signal indicative of the temperature in the subphase of the trough 10 to the controller 72. The controller 72 compares the current temperature with the desired temperature, set by the user at reference temperature set point 94, and generates an error signal if the current temperature deviates from the desired temperature. The error signal triggers the actuator 73, i.e. the thermoelectric cooling devices, to equalize the two temperatures by increasing or decreasing the temperature in the trough by a predetermined amount.

The illustrative temperature control system provides efficient and accurate temperature control for the formation process without incurring high costs. The illustrative design allows the use of high capacity thermoelectric cooling devices to efficiently control the temperature of the trough. The illustrative design is also less expensive than current commercial models and allows for relatively easy implementation of future upgrades.

Figure 5:
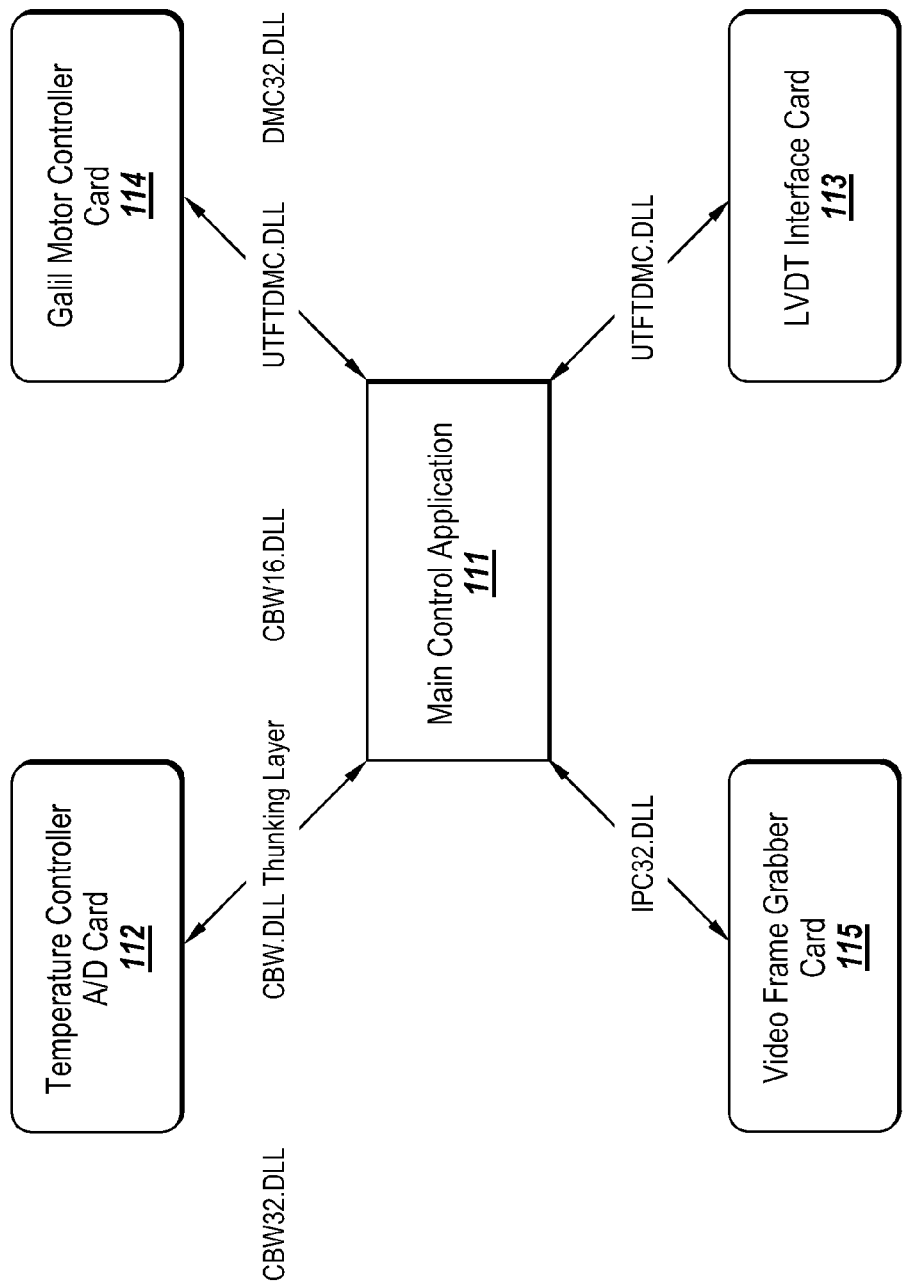
FIG. 5 is a block diagram of the software modules in the integrated trough system of the illustrative embodiment.

The integrated system of the illustrative embodiment further includes an enhanced software system allowing for the simultaneous execution of several tasks, including control of the ordered structure, temperature control and image acquisition. FIG. 5 is a block diagram of the software modules forming the enhanced software system of the illustrative embodiment. FIG. 5 further illustrates the data flow path between the main control application program 111 and various software modules, which store instructions for performing particular tasks in dynamically linked libraries (DLL). To perform a particular task, the main control application program 111 calls the DLL in a respective linked card and executes the instructions stored therein. The image acquisition software is a three-dimensional imaging system allowing a user to gather two-dimensional data sets at different time points during a pressure-area experiment. The software system 110 includes a main control application 111, a temperature controller card 112 for interfacing with the temperature control system described above and a video frame grabber card 115 interfacing with the video camera 52 for controlling video acquisition and image processing. Video frame grabbing refers to the step of converting analog video signals of an object to digital signals that a computer can process. The video frame grabber card 115 provides instructions for digitizing images of the ordered structure in the trough in real time and storing the images in the memory of the imaging board 54. The software system 110 further includes an LVDT interface card 113 and a microprocessor-based motion controller card 114, such as a motor controller card from Galil Motion Control, Inc. for controlling movement of the microscope 51 and/or the automated ordered structure transfer device 82 with respect to the trough 10.

Figure 6:
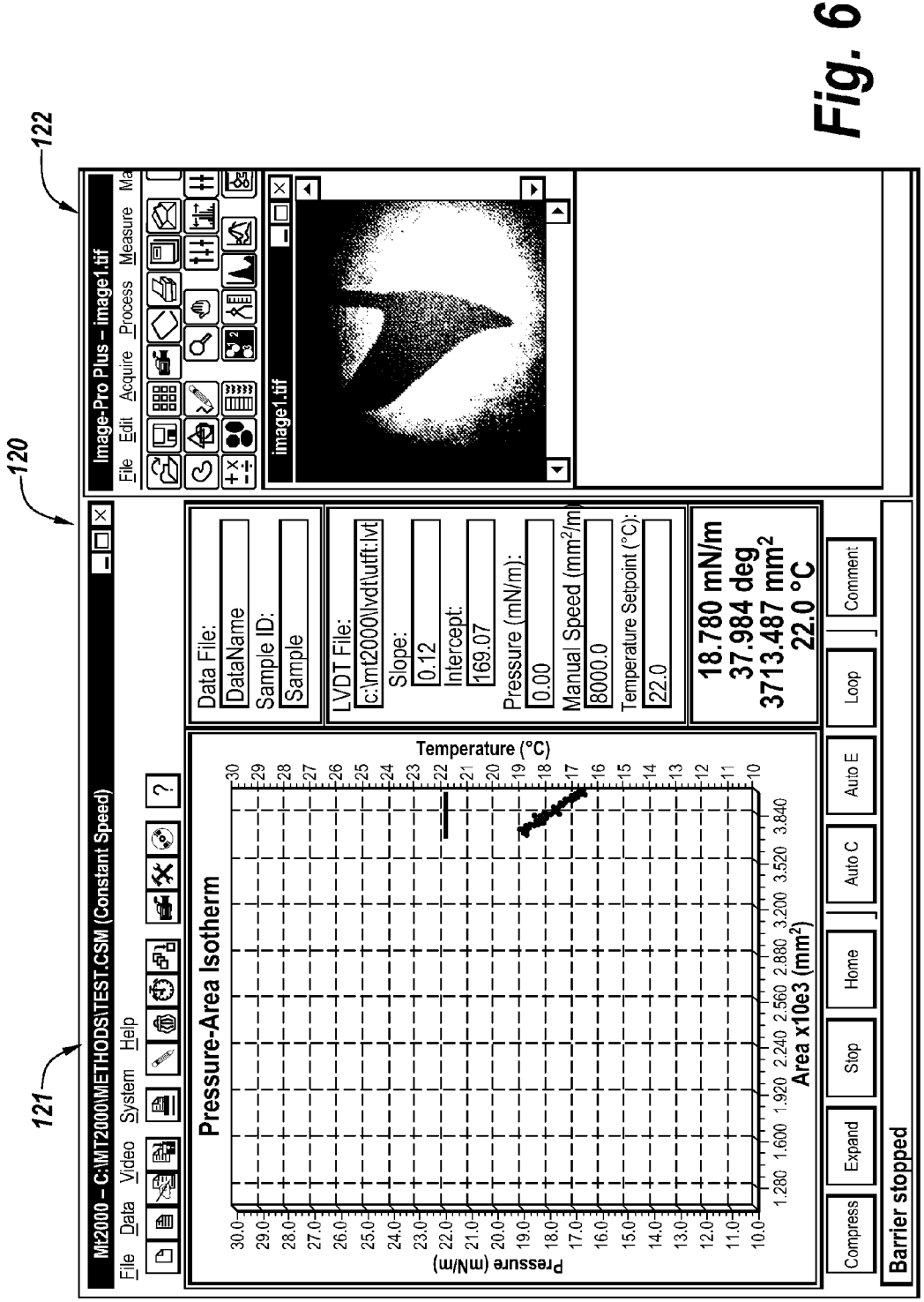
FIG. 6 illustrates a graphical user interface generated for viewing and analyzing a monolayer formed in the trough according to the illustrative embodiment.

FIG. 6 illustrates a graphical user interface 120 generated by the software system of the present invention. As shown, the enhanced software allows ordered structure parameters, as well as an image of the ordered structure to be displayed simultaneously. The image acquisition software of the illustrative embodiment is a three dimensional (3-D) imaging system. This allows the user to gather two-dimensional data sets at different time points during a pressure-area experiment, e.g., during the formation of an ordered structure. The three-dimensional imaging software utilizes the Image-Pro Plus (from Media Cybernetic) image analysis software for acquiring and analyzing images of the ordered structure formed in the trough 10, though one skilled in the art will recognize that any suitable image processing software may be utilized. This software provides an application programmer's interface for remote control of the video frame grabber function from within the software system. The ordered structure's physical parameters as well as image data may be viewed simultaneously through the graphical user interface displayed on the PC monitor. Each image is time-stamped and stored along with the ordered structure's physical parameters. As illustrated in FIG. 6, the ordered structure parameters are displayed in a first application window 121, whereas the image of the ordered structure, captured by the image acquisition and processing system of the illustrative embodiment, is displayed in a second application window 122. According to an alternate embodiment, video images recorded by the video recorder are incorporated directly into the first application window 121 and displayed.

The imaging software allows the user to configure and control the image acquisition conditions. Upon starting an experiment, live capture from the microscope's video camera is enabled. The user is prompted to set the desired video image capture interval. The user is permitted to provide custom interval settings or to use the software's default settings. At this point the user can choose between a static time-delay between acquisitions (for example, sampling every minute), a variable time delay, or alternatively a manual time delay (capture on demand). The amount of RAM and the size of the hard drive installed in the computer system 67 determine the total number of images captured during an experiment.

In an embodiment, the invention pertains to a method of forming ordered structures of amphiphilic molecules (e.g., proteins), by applying amphiphilic molecules to a subphase (e.g., an gas-aqueous interface, e.g., an air-water interface) and compressing them to an appropriate pressure, such that ordered structures (e.g., crystals and other nano- or micrometer scale ordered arrays) with desired dimensions and characteristics are formed. The technique is simple and versatile for use with most amphiphilic molecules that can be spread at a subphase (e.g., an air-water interface). The technique entails molecular engineering based upon compressing a population of amphiphilic molecules on an interface to an appropriate pressure. Briefly, a population of amphiphilic molecules is applied to a subphase (e.g., at an air-aqueous interface of the monolayer trough). The planar membrane may be compressed by means of a barrier. Further compression of the planar membrane, e.g., monolayer, toward or beyond its critical point (e.g., their limiting area/molecule), result in the formation of two- and/or three-dimensional mono- or multilayered ordered structures that may be similar to crystal structures observed in bulk.

Amphiphilic molecules, such as proteins, can be applied, e.g., spread, at the air-water interface from a detergent solution onto a lipid film. Other methods of applying the protein include applying a native preparation of lipid membrane or proteoliposomes preferably including over-expressed amounts of the desired protein. Alternatively, the protein can also be applied using reconstituted protein-lipid liposome preparations. Preparation of the proteoliposomes is done by the detergent dialysis technique of Mimms et al., using an appropriate protein to lipid ratio (*Biochem.* 20, 833-840 (1981)).

This invention is further illustrated by the following examples which should not be construed as limiting. The contents of all references and published patents and patent applications cited throughout the application are hereby incorporated by reference.

EXEMPLIFICATION OF THE INVENTION

Example 1

Direct Visual Evidence for the Formation of Ordered Structures, e.g., Large Ordered Domains, of a Membrane Proteins at an Air-Aqueous Interface In this example, a unique ability to grow ordered structures of a membrane protein on a liquid in a fast and controlled fashion is demonstrated. The membrane protein cytochrome c oxidase (COX) from beef heart was chosen as a model membrane protein to elucidate the feasibility of the technique. The structure of COX has been extensively studied in different laboratories. The structure of the metal sites of COX was determined to 2.8 A resolution by x-ray analysis (Tsukihara, T., et al. *Science* 269, 1069-74 (1995)). Crystal structure information at intermediate resolutions is available of tetragonal or hexagonal bipyramidal crystals that diffract x-rays to 5 Å (Shinzawa-Itoh, K., et al. *J. Mol. Biol.* 246, 572-575 (1995)) and 8 Å (Yoshikawa, S. et al. *PNAS*, 85, 1354-1358 (1988); Yoshikawa, S., et al. *J. Crystal Growth*, 122, 298-302 (1992)) respectively. The structure of COX is also known, at low to intermediate resolution, from image processing of electron micrographs of two-dimensional crystals of the protein (Frey, T. G. *Microscopy Research and Technique* 27, 319-332 (1994)). Two such crystal forms have been reported, one consists of dimers (Henderson, R. et al. *J. Mol. Biol.* 112, 631-648 (1977)) and a second consists of monomers of COX (Fuller, S. D. et al. *J. Mol. Biol.* 134, 305-327 (1979)). In both cases, these in-situ crystals of the protein are so small that they cannot be resolved with high resolution electron microscopy. Instead, researches have used elaborate image processing techniques to indirectly provide insight into the structure of the protein. The dimer crystal form of COX has been most extensively studied. Cryoelectron microscopy analysis of Valpuesta et. al. extended the earlier structure information of Henderson and coworkers to 8-10 Å resolution in the plane of the membrane and to 15 Å perpendicular to it (Valpuesta, J. M. et al. *J. Mol. Biol.* 214, 237-251 (1990); Henderson, R. et al. *J. Mol. Biol.* 112, 631-648 (1977)). These results revealed that the two-dimensional space group for the dimer is pgg, the two-sided plane group p22$_1$2$_1$, with cell dimensions a=95 Å, b=125 Å, γ=90°. The crystals of COX monomers were characterized by Fuller et al. (Fuller, S. D. et al. *J. Mol. Biol.* 134, 305-327 (1979)). They concluded that the crystals are packed in a single layer. The two-dimensional plane group is pg with unit cell constants of a=68 Å and b=174 Å, and corresponding to the two-sided space group p12$_1$.

In the following example, the process for lining up COX molecules at an air-aqueous interface, is described. Formation of ordered structures of the protein is demonstrated by digital laser fluorescence video microscopy. It is also shown the shape of these domains often appears to be directly related to the known configuration of the individual protein molecules. Unexpectedly, three-dimensional ordered structures of the protein at the air-aqueous interface were also formed. The degree of orientational order of these microstructures by parallel x-ray as well as electron crystallography is currently being investigated. The following example is a preliminary characterization of the factors that govern formation of ordered domains of the protein at the air-aqueous interface.

Techniques

Chemicals and Biochemicals

Biotinilated cytochrome c (B-CC), and fluorescein isothiocynate conjugated avidin (FITC-A) were from Sigma. Fluorescein isothiocyanate conjugated streptavidin (FITC-SA) was purchased from Biomeda Corp. (Foster City, Calif.). Fluorescently labeled lipids L-α-Phosphatidylethanolamine-N-(lissamine rhodamine B sulfonyl) (Egg) (R-PE), and 1-Acyl-2-{12-{(7-nitro-2-1,3-benzoxadiazol-4-yl)amino}dodecanoyl}-sn-glycero-3-Phosphatidylethanolamine (NBD-PE) were from Avanti Polar Lipids (Alabaster, Ala.).

Membranous COX was a generous gift of Professor T. G. Frey, San Diego State University. The membranes were prepared using the method developed by Frey et al. (*J. Biol. Chem.* 253, 4389-4395 (1978)). The material was in the form of proteoliposomes, with a high concentration of protein, 10-15 mg protein/ml, and approximately 3-5 mg phospholipid/ml (T. G. Frey personal communication). They were suspended in 10 mM potassium phosphate buffer, pH 7.2, including 0.25 M sucrose. The material was received on dry ice and transferred to −80° C. upon arrival. Samples for crystallization experiments were prepared by rapidly thawing the stock under flowing water at room temperature. Aliquots were made in 1.5-ml microfuge tubes after diluting the stock ten times. The tubes were often rapidly frozen under liquid nitrogen, prior to their transfer to −80° C. for storage. An aliquot of the proteoliposome suspension was thawed, under running water at room temperature, immediately before the crystallization experiment, and used within the same day.

Preparation of Protein Microdomains at an Air-Aqueous Interface

A suspension of the proteoliposomes was spread at the air-aqueous interface of the Micro-Trough MT-100 equipped for digital laser fluorescence video microscopy. The proteoliposomes were spread against an increasing surface pressure by using a modified form of the procedure described earlier by Verger and Pattus (*Chemistry and Physics of Lipids* 16, (1976)). Prior to each experiment, the trough was assembled by using clean components, including the Kalrez barriers, the quartz plate comprising the bottom of the trough, the Teflon rings comprising the side walls and the O-ring seals that prevent subphase leakage. Surface pressure was measured by using the Wilhelmy method. The Wilhelmy plate was cut from Whatman No. 2 paper. A new plate was used for each experiment. The trough was filled with a hypotonic buffer including 10 mM phosphate, pH 7.2. The buffer was prepared fresh daily by using a continuos flow ultra pure water system and stored in a glass container. A clean sintered glass slide was inserted into the subphase and made wet with the buffer to about 1 cm above the water line. The proteoliposomes, with their internal as well as external volumes composed of a hypertonic buffer including 10 mM phosphate and 0.25 M sucrose pH 7.2, were deposited onto the pre-wetted areas of the glass slide via a glass micropipette.

The working area of the trough was kept constant, around 40-44 $cm^2$ during the spread of the proteoliposomes. Upon encountering the hypotonic subphase buffer, the proteoliposomes lysed and spread as a planar membrane at the air-aqueous interface. Formation of the planar lipid-protein film was evidenced by an abrupt rise in surface pressure. Excess amounts of the proteoliposome suspension were delivered sequentially, to a final bulk concentration of 50-150 µg/ml in protein and 15-50 µg/ml in lipid in a total volume ranging between 6-12 ml. An equilibrium pressure was achieved between the spread film and the unlysed proteoliposomes where further additions of proteoliposomes did not cause a substantial increase in surface pressure. The range of the equilibrium pressure varied between 20 to 38 mN/m. Subsequent to establishing the equilibrium, excess unlysed proteoliposomes were washed away from the lipid-protein film, by several vigorous exchanges of the subphase with fresh hypotonic buffer. A 5-10 mN/m drop in surface pressure was observed, during the removal of the proteoliposomes. The lipid-protein film was compressed at a rate of 500 $mm^2$/min, from approximately 40 to 11 $cm^2$, to a maximum density corresponding to pressures between 35-45 mN/m.

Preparation of Ordered Protein Microdomains for Fluorescence Imaging: Double Labeling of the Lipids and Protein.

The lipid molecules in the lipid-protein film were probed with the fluorescent lipid probe R-PE. A dilute film of about 1 pg of R-PE was spread from a dichloromethane solution on a clean subphase including 10 mM phosphate, pH 7.2. Subsequent to the evaporation of the solvent the proteoliposomes were spread and the excess unlysed material was removed as described above. COX was fluorescently probed, at the air-aqueous interface, with FITC by producing a ternary complex, between COX, B-CC and FITC-SA (FITC-A). The complex was formed in two steps. Initially, a binary complex was formed between COX and B-CC, by injecting a solution of B-CC in buffer, through the lipid-protein film into the subphase to a final concentration of 50-100 µg/ml. After an incubation period of 5-20 minutes, excess B-CC was washed away from the film by several exchanges of the subphase with fresh buffer. In the next step, a ternary complex was formed between COX-B-CC and FITC-SA (FITC-A), by injecting a solution of the FITC-SA (FITC-A), through the lipid-protein film to a final concentration of 10-20 µg/ml. After an incubation period of 5-20 minute, unbound FITC-SA (FITC-A) was removed in the same manner as described for the removal of unbound B-CC.

Digital Fluorescence Video Imaging and Image Processing System

The Micro-Trough MT-100 was mounted on the stage of an Olympus IMT-2, equipped with epi-illumination optics. Fluorescence emission from both the rhodamine as well as the FITC probes was excited with the 488 nm line of an air-cooled argon laser (Ion Laser Technology Systems, Salt Lake City, Utah). Using an Olympus DPlan ×10 (N.A. 0.25) or CDPlan ×40 (N.A. 0.50) ultralong working distance objectives the fluorescent domains were imaged at the air-aqueous interface, as well as throughout their transfer to solid supports. The ×40 objective was equipped with a 0.0-2.0 mm correction collar that facilitated high resolution imaging throughout the height of the subphase in the trough. By adjusting the objective collar to an appropriate height, the film was visualized at the air-aqueous interface, through a 1-mm quartz plate located at the bottom of the MT-100, and a 0.5-0.7 mm depth of subphase. Films were transferred to a solid support at the air-aqueous interface or alternatively were deposited onto the quartz plate at the bottom of the trough. Deposition of the film onto the solid substrate could be visually monitored throughout the transfer process by using the same optics. Fluorescence emission from both the FITC and rhodamine probes passed through a 505-nm dichroic long pass filter (505DCLP) (Chroma Technology Corp., Brattleboro, Vt.), and subsequently through a 515-nm long pass emitter (OG515) (ibid.). Digital laser fluorescence video image acquisition and processing was done by using the system described above.

Preparation of Specimens for Electron Crystallography

Specimens for electron crystallography analysis were prepared from planar membranes of COX both in the presence of the ternary protein-ligand complex as well as in its absence. This strategy allowed for the effect of the interaction of the ligand (B-CC) and the fluorescent protein probe (FITC-SA) on the crystal structure of COX to be determined. The lipids in the lipid-protein film were labeled with either the lipid probe NBD-PE or R-PE as described before. The ordered structures were transferred from the air-aqueous interface to 200 mesh copper electron microscope grids by horizontal deposition. The grids were pre-coated with either a hydrophilic (silicon oxide) or hydrophobic (carbon) film. They were placed horizontally on top of the ordered structure for 5-10 minutes, and removed from the interface with a pair of tweezers. The grids were air-dried prior to their transfer to a grid box for storage. The stored ordered structures were analyzed within 30 days from their preparation.

Electron Microscopy and Diffraction Analysis

Preliminary electron microscopy and diffraction analysis experiments made use of the MRSEC Shared Experimental Facilities supported by the National Science Foundation under award number DMR94-00334. Electron micrographs from unstained ordered structure were recorded at room temperature at 200 kV in a Joel 200CX microscope. Significant beam damage to the ordered structure was observed under these experimental conditions. In order to avoid prolonged ordered structure irradiation during the recording of an image on film, images were recorded at video rate on a videocassette. Diffraction patterns as well as bright and dark field images were later captured from the videotape by using the digital image processing system described in subsequent sections. However, since the images still exhibited considerable beam damage, follow up experiments are postponed to the use of a high voltage, low-temperature electron microscope facility.

Subsequent electron micrographs and diffraction patterns were recorded from unstained ordered structures, in an AEI-EM7 high-voltage electron microscope, equipped with a Gatan 626-cryotransfer stage. The images were recorded at room temperature, on MRF32 film at 1200 kV. The microscope was equipped with a Pulnix intensified CCD camera, which produces images at video rate from low beam dose rates at about $2 \times 10^{-11}$ amp. This allows scanning the specimen and focusing using minimal irradiation. The selected area was located by scanning in diffraction mode with negligible electron exposure at approximately $2 \times 10^{-12}$ amp. The low dose exposure is estimated to be approximately 10 electrons/$Å^2$. When an area was found that produced a high-resolution zone-axis pattern, the beam was turned off, film was transported into the camera, and the beam was turned on only when the camera shutter had opened. Electron micrographs were obtained subsequently from the selected area. This procedure minimized electron damage to the crystals prior to the recording of the diffraction pattern. The film was developed for four minutes in XRD developer at 20° C., which gave an acceptable density at the low exposure. Subsequent to the recording of an electron diffraction pattern, a bright field image of the same selected area was recorded on film.

Results And Discussion

The structure of COX was analyzed qualitatively by fluorescence imaging as well as electron crystallography. Digital laser fluorescence video imaging revealed formation of ordered structures of COX in planar membranes spread at an air-aqueous interface.

Ordered structures were observed by fluorescence, in planar membranes spread from proteoliposome preparations of COX at the air-aqueous interface. The proteoliposomes were spread against an increasing surface pressure in order to minimize surface denaturation of the protein. The planar protein-lipid membrane (which contained the ordered structures) was stained with two different labels to bring out the contrast between the lipid and protein species. The protein was stained with FITC-SA (FITC-A) bound to a B-CC-COX complex. The lipids were stained with R-PE. All films reported in these studies were formed at ambient temperature (22±2° C.), over a buffer subphase including 10 mM phosphate, pH 7.2. The protein ordered structures were observed using an ×10 or ×40 objective. They appear green in an orange background made by the fluorescent lipid probes partitioning the lipid domains of the film. A 0.2 second on chip integration time was used on the camera to produce these images. The ordered structures reported here were observed at a surface pressure corresponding to 16 mN/m. On the left in FIGS. 7A, 7C, and 7E, it was demonstrated by fluorescence some of the many ordered structures that were generated. These ordered structures exhibit several distinct features. Most notable is the remarkable similarity between the shape of these ordered structures and the images of the crystals of COX calculated from electron microscopy analysis as shown on the right in FIGS. 7B, 7D, and 7F.

Figure 7A:
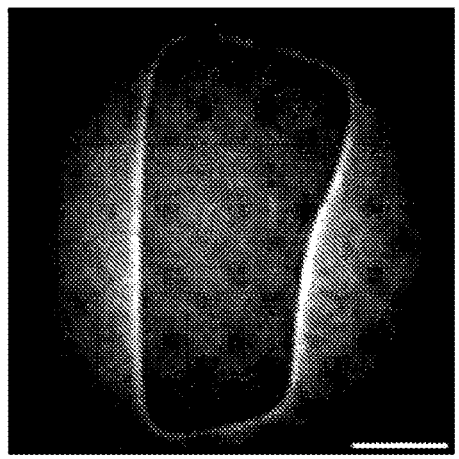
FIG. 7A is a digital image of an ordered structure generated by methods of the invention, specifically a fluorescence image of an ordered structure of COX in a planar membrane spread at an air-aqueous surface.
Figure 7B:
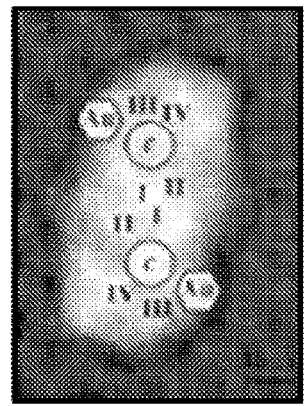
FIG. 7B is an image of a single COX dimer calculated from electron micrographs of frozen hydrated crystals

The fluorescence micrograph in FIG. 7A provides direct visual evidence of the morphology of a rectangular ordered structure consistent with the known shape of a dimer molecule. In comparison, FIG. 7B shows an image of a single COX dimer calculated by Frey and coworkers, from electron micrographs of frozen hydrated crystals (Frey, T. G. & Murray, J. M. *J. Mol. Biol.* 237, 275-297 (1994)).

Figure 7C:
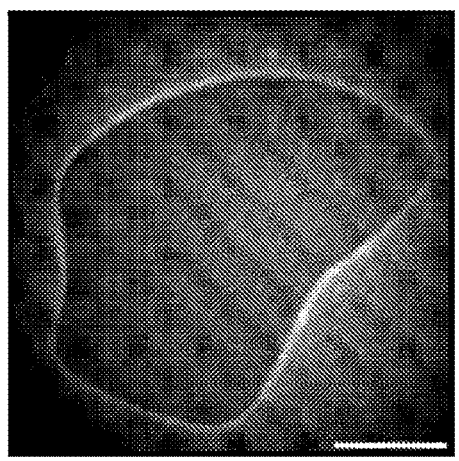
FIG. 7C is a digital fluorescence image of another ordered structure of COX in a planar membrane spread at an air-aqueous surface with a COX domain resembling the shape of the protein in its monomeric form.
Figure 7D:
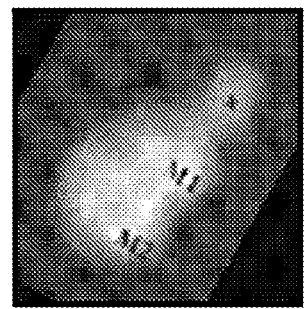
FIG. 7D is an image of COX domain in its monomeric form calculated from electron micrographs of frozen hydrated crystals.
Figure 7E:
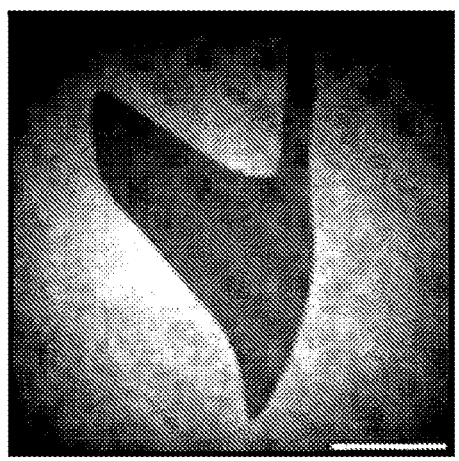
FIG. 7E is a digital fluorescence image of another ordered structure of COX in a planar membrane spread at an air-aqueous surface.
Figure 7F:
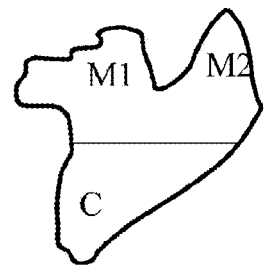
FIG. 7F is an image of COX domain with a y shape crystal form of the protein based on a three-dimensional reconstruction calculated from electron micrographs of frozen hydrated crystals.

The monomer crystals of the protein have a different appearance than the dimers. Fuller et al. characterized this crystal form. The shape of the molecule is represented by a lower case letter y from their balsa wood model. FIG. 7C is a fluorescence micrograph of a COX domain resembling the shape of the protein in its monomeric form, calculated by Frey and Murray (FIG. 7D). FIG. 7E is a protein domain observed by fluorescence that is remarkably similar to the y shape crystal form of the protein (FIG. 7F), taken from the three-dimensional reconstruction of Fuller et al.

The orientation of proteins at the air-aqueous interface sometimes appears to be perpendicular to the expected orientation of the protein molecules in the cell membrane (see FIGS. 7 A-F). It is not clear what factors govern the orientation of the protein at the air-aqueous interface. The protein molecules may re-orient at the air-aqueous interface during their spread at low packing densities. Alternatively, the orientation of the domains may be indicative of the formation of multilamellar structures at the air-aqueous interface. This effect can be studied by measuring the thickness of the film at different packing densities, may be better understood.

Other forms of COX domains were also observed at the air-aqueous interface. The detailed shape of these domains provides further insight into several other distinct features of the structure of the COX molecule. Of particular interest in some fluorescence micrographs, was a hole or slit that appeared as an isolated lipidic phase (orange) within the protein domain. The hole or slit may be attributed to the presence of a cleft in the dimer that separates its two monomer halves. The cleft in the dimer was previously suggested by Costello and Frey (*J. Mol. Biol.* 162, 131-156 (1982)). The trigonal symmetry of the hole as shown in certain contours of the domains was also shown. Sometimes, the micrographs show COX structures which show the domains split apart, consistent with earlier electron microscopy results of Frey and coworkers.

In producing the micrographs, image enhancement was used to help the eye differentiate between the fluorescent molecules. It is believed that important information may be inferred from these colors. For example, in image enhanced micrographs, areas around the periphery of the protein domains sometimes appear to have a darker green contrast than in the middle. The darker contrast is attributed to self-quenching of fluorescein molecules in a densely packed protein array. Also, of interest in some of these micrographs is the presence of a bright orange-red halo around the protein ordered structures (FIGS. 7A-7F). The halo may be indicative of the existence of lipid-embedded domains in the individual COX molecule. Thus, the enhancement of contrast in the halo is probably due to energy transfer from bound FITC protein complex to rhodamine tagged lipid probes residing within a close proximity of the protein in the lipid-embedded domains. The existence of the lipid-embedded domains was suggested by Frey from observation of ice-embedded specimen of COX crystals. Similar observations were made by Brisson and Unwin in electron micrographs of specimen of acetyl choline receptor frozen in vitreous ice, showing denser protein domains contrasted by less dense ice or lipid domains (Brisson, A. & Unwin, P. N. T. *Nature,* 315, 474-477, (1985)).

The excellent contrast between the protein ordered structures and lipid domains, in the fluorescence micrographs in FIGS. 7A-7F, is a result of quenching of background fluorescence due to energy transfer from FITC to the rhodamine probes. Specifically, enhancement of contrast was due to quenching of fluorescence that was originated from those FITC molecules that were either nonspecific ally bound to the lipids or low concentrations of unbound molecules floating in the subphase, below the lipid film. Confirming this hypothesis, in control experiments, much lower contrast was observed, when the film was probed with FITC-SA in the absence of the rhodamine labeled lipid. The protein ordered structures were hardly visible in the somewhat homogeneous green planar membrane, due to substantial background fluorescence. Low contrast was also observed when the planar membrane was probed with a lipid probe only. The somewhat homogeneously orange appearance of these films was probably due to the rhodamine lipid probes that partitioned the lipid domains as well as those lipid probes that stained the protein molecules. Under certain conditions, in these single probe studies, dark patches of loosely packed protein domains, with no specific symmetry were also observed.

The ordered structures, e.g., solid phase domains are formed at the air-aqueous interface probably due to a long-range orientational order. Weis and McConnell showed that such an order is essential for formation of chiral crystals on compression of lipid monolayers of dipalmitoylphosphatidylcholine at an air-water interface (Weis, R. M. & McConnell, H. M. *Nature*, 310, 47-49 (1984)). It is speculated that a high protein/lipid ratio in the proteoliposome may facilitate the formation of the ordered structures. Pattus and co-workers in spreading of biomembranes at an air-water interface report that the surface density of the protein increases, when membranes are spread at higher surface pressures (Pattus, F. et al. *Biochim. Biophys. Acta* 507, 71-82 (1978)).

Digital laser fluorescence imaging reveals formation of three-dimensional ordered structures on compression of a lipid-protein film of COX at an air-aqueous interface. The detailed shape of the protein ordered structures is a sensitive function of the packing density within the lipid-protein film. At higher pressures (e.g., about 40 mN/m), a slight drop in pressure during the pause was observed. This can be seen as a point of discontinuity in the pressure-area isotherm. A reduction in size of an ordered structure, due to a compression induced increase in the packing density of the molecules was observed. A remarkable feature of the compression of the lipid-protein film is a critical density point around 34 mN/m. At this point one observes by fluorescence a drastic rearrangement of the molecules in the film. Further compression of the film beyond the critical density point results in formation of small (20-50 μm diameter) ordered structures with a three-dimensional (3-D) appearance. The three-dimensional shape for these ordered structures, was particularly noticeable after the ordered structures were transferred to a solid substrate. The three-dimensional shape of the domains was noted with the out of focus depth in these micrographs. New x-ray microdiffraction technologies that incorporates an intense microbeam source of radiation is being used to determine the degree of structural order in these three-dimensional ordered structures.

It is interesting to note that, in their earlier studies on the brush border membrane, Demel et al. attribute a surface pressure of 35 mN/m to the lateral pressure in the native membrane (Demel, R. A. et al. *Biochim. Biophy. Acta* 406, 97-107 (1975)). By analogy, a correlation between the critical density observed around 34 mN/m in the planar membrane was drawn to the to the lateral pressure of the native membranes of COX.

Recently, Rein ten Wolde and Frenkel suggested an enhancement of protein crystal nucleation by critical density fluctuations (*Science* 211, 1975-1978 (1997)). Their numerical simulation for certain globular proteins suggests that close to a critical point, the free-energy barrier for crystal nucleation is strongly reduced and hence, the crystal nucleation rate is increased by many orders of magnitude. An implication of their findings is that one can selectively speed up the rate of nucleation, without increasing the rate of crystal growth, or the rate at which amorphous aggregates form. This can be achieved in solution by changing for example the composition of the solvent. The formation of cholesterol crystals at an air-aqueous interface provide direct evidence on the extension of this rule to a system in two-dimensions. In that example, a direct correlation between supersaturation beyond a metastable critical density point and the crystal nucleation process was noted. Specifically, no crystals were formed by rapidly compressing the monolayer way beyond the metastable critical density point. In this example, the formation of a certain population of domains immediately above a critical density point was observed. It is therefore, reasonable to expect that the methods of the invention provide an ideal framework to extend the general theoretical derivations of Rein ten Wolde and Frenkel to protein systems in two-dimensions.

Example 2

Electron Microscopy and Electron Diffraction of Ordered Domains Prepared at an Air-Aqueous Interface Ordered structures of the protein COX were formed at an air-aqueous interface for structure analysis by electron crystallography. The ordered structures were transferred to hydrophobic (carbon-coated) or hydrophilic (silicon oxide coated) grids. Two different types of specimen preparations were used for comparative analysis. In certain specimens, a complex was made between the protein, B-CC and FITC-SA. However, these probes were excluded in a majority of specimen preparations in order to eliminate the effect of bound ligands on the structure of the protein. In all specimen ordered structures, the lipids were probed with the fluorescently tagged lipid R-PE. Inclusion of the lipid probe facilitated visual monitoring of the ordered structure during its transfer to the grids. The electron microscope studies reported here were done on unstained specimen, at room temperature (22±2° C.), by using either 200 or 1200 kV electron beams.

Consistent with the fluorescence studies, direct visual evidence on the presence of ordered structures was obtained by electron microscopy. The protein ordered structures that were deposited on the grids were up to 110 μm$^2$ in area. Although these domains were significantly smaller than those observed at the air-aqueous interface, they appeared to present the same overall morphology as their larger counterparts. It is not uncommon to obtain a smaller domain size on films transferred to a grid in comparison to that at an air-aqueous interface. In preparation of electron microscope grids from crystals of a soluble protein on a lipid monolayer, Darst et al. report a similar behavior (*Biophys. J.* 59, 387-396 (1991)). They speculate that the smaller crystals are derived from the larger domains at the air-aqueous interface, but are broken apart during the transfer process due to the stresses involved therein.

The morphology of these domains that were transferred to the grid is reminiscent of the three-dimensional representation of a single monomer or dimer molecule as explained above. In some cases, typical rectangular or y-shaped domains were observed. Another remarkable feature of the electron micrographs is the appearance of two different regions within the protein ordered structure. This is consistent with the observation of a bright halo around the protein in some fluorescence micrographs shown in FIGS. 7A-7F. The brighter contrast observed around the protein ordered structure was attributed to the presence of less dense lipid-embedded domains around single protein molecule. The darker contrast observed in the central regions is probably due to the presence of densely packed protein molecules. In this example, it was observed that the densely packed regions were more prone to electron beam damage, than the less dense lipid-embedded areas surrounding the protein.

Electron diffraction analyses of the ordered structures of COX provide evidence on different features of the specimen preparation technique. In certain areas of the grids, distinct diffraction spots were observed, that were extremely resistant to beam damage. The lattice spacing calculated from such diffraction patterns was on the order of 5-10 Å which is smaller than the larger distances expected from a protein molecule (typically 100 Å). These results indicate the presence of small organic or inorganic crystals such as salt or silicates in the specimen. At the bottom are bright field electron micrographs of the selected area, showing an epitaxial growth of the crystalline material. These micrographs were taken from films transferred to a silicon oxide grid around 18 mN/m. Occasionally, during the scan of the specimen, sharp diffraction spots were encountered which rapidly faded away before being recorded on film. In view of their sensitivity to beam damage, these spots are attributed to the presence of crystalline protein domains that deform or dehydrate under the electron beam. This example may be repeated by preparing frozen-hydrated specimens for cryoelectron diffraction analysis of the protein. However, if the protein forms have a three-dimensional morphology, they will not diffract electrons. Thus, x-ray diffraction analysis by using an intense microbeam source of radiation may also be used. The remarkable long-range orientational order observed in these ordered structures, suggests that these strategies may provide a means to determine, for the first time, the three-dimensional structure of the COX in ordered domains made in a natural membrane at an air-aqueous interface.

Conclusions

Formation of ordered two-dimensional or three-dimensional structures at an air-aqueous interface has not been previously reported for any membrane protein. The experiments discussed here demonstrate the feasibility of a novel approach for fabrication of ordered ordered structures of the membrane protein COX at an air-aqueous interface. These studies lead to the following conclusions, (i) At intermediate pressures, corresponding to 10-30 mN/m, and below a critical density point, the membrane protein COX arranges at the air-aqueous interface in large, ordered forms. The detailed shape of the protein ordered structures often appears to be directly related to the known configuration of individual protein molecules both in their monomer and dimer forms, (ii) At high pressures beyond a critical density point, the formation of a different population of domains consisting of smaller three-dimensional ordered structures were observed.

This example provides evidence of the presence of ordered structures. This was shown by the fast fading spots that were observed in electron diffraction analysis of unstained specimen taken at room temperature. In two different lipid systems, ordered structures were shown to grow at the air-water surface.

Electron diffraction analysis of the protein ordered structures will continue in order to determine the degree of orientational order in the protein domains. These studies are conducted at cryogenic temperatures, to reduce radiation damage to the protein. The results do not rule out the possibility that the large domains, formed below the critical density point, may also be three-dimensional ordered structures. Parallel x-ray diffraction studies, by using an intense microbeam source, will allow the probing of the structure of this population of ordered structures.

Fabrication of ordered two-dimensional and three-dimensional domains from membranes is not only relevant to the rational design of drugs with molecular modeling based on high-resolution three-dimensional structure of the target protein, but it may also play a key role in proteomics to accelerate drug discovery via structure activity relationships (SAR). The fluorescence imaging studies, provide direct visual evidence on binding of a high affinity ligand, such as the cytochrome c to COX. This was evidenced by a qualitative fluorescence assay based on fluorescence visualization of formation of a ternary complex between COX, B-CC and FITC-SA. This example showed that ordered protein ordered structures can be formed both in the absence of the ligand as well as in the presence of a ligand bound protein complex.

Example 3

Direct Visual Evidence for Formation of Ordered Two-Dimensional Ordered Structures of the Multidrug Resistance P-Glycoprotein In another system, comprised of the multidrug resistance P-glycoprotein (P-gp), the formation of large ordered domains of the protein in its natural membrane was demonstrated. Non-random distribution of cell surface P-glycoprotein (P-gp) in monolayers spread from multidrug resistant MCF-7 $Adr^R$ and MCF-7 sensitive cell lines was shown. Cell membrane vesicles were prepared according to the method of Cornwell et al. (*J. Biol. Chem.* 261, 7921-28 (1986)). Monolayers were spread from vesicles in a hypertonic buffer including a high concentration of sucrose. The vesicles were spread at the air-aqueous buffer interface of the Micro-Trough MT-100, on a hypotonic buffer in the same manner as it was discussed earlier for COX. Spreading of the monolayer was monitored by observing an increase in the surface pressure of the spread film at a constant area. P-gp was probed with a fluorescent derivative of verapamil, a calcium channel blocker that binds to P-gp. Fluorescence microscopic observation of P-gp in monolayers spread from drug resistant cell membranes suggests strong long-range orientational order of the protein in monolayer, induced by compression. This led to formation of densely packed domains of the protein, which may eventually lead to its crystallization. No such domains were observed in control experiments in monolayers spread from drug-sensitive cell membranes. This may be due to presence of negligible amounts of protein in drug-sensitive MCF-7 preparations in contrast to drug-resistant membranes.

The total amount of P-gp in the drug resistant MCF-7 $Adr^R$ plasma membrane preparations is estimated to be as little as 2%. These results therefore suggest that extremely high concentrations of the protein may not be essential for fabrication of crystals by monolayer compression.

The structure of P-gp was recently solved to 25 Å resolution (Rosenberg, M. F. et al. *J. Biol. Chem.* 272, 10685-94 (1997)). The shape of the large domains we produce was remarkably reminiscent of the molecular outline of P-gp proposed by Rosenberg et al. The aqueous pore, open at the extracellular face of the membrane, was clearly evident in both images. The fluorescence micrograph also provides evidence on the shape of the thumb-shaped domains (TMD) as well as the nucleotide binding domains (NBD).

Two-dimensional crystallization within the membrane, in comparison with two-dimensional and three-dimensional crystallization from solution has some advantages. Since the protein does not dissociate from the lipid bilayer, the native asymmetry of the membrane is maintained. The restricted freedom of movement in the planar membrane means that the chances of lattice formation are higher than for crystallization from an isotropic solution. Usually, the protein is not exposed to high levels of detergent and is therefore more stable. In bilayers, possibilities for improving the crystallization conditions by varying experimental parameters are limited. However, monolayer compression provides the necessary tool for rearranging the molecules in both natural as well as reconstituted membranes.

Example 4

Direct Visual Evidence for the Nucleation of Cholesterol Crystals at an Air-Water Interface Near a Metastable Critical Density Point Cholesterol appears in animals in certain cell membranes, bound to lipoprotein or incorporated in the bile micelles. Crystals of cholesterol monohydrate deposit when cholesterol levels are unusually high. In bile, these crystals stack up to form gallstones. Cholesterol monohydrate crystals also occur in arherosclerotic lesions. The cholesterol molecule is an ampiphile. It is almost hydrophobic except for the presence of a hydrophilic C(3) hydroxyl group. This amphiphilic character of the molecule allows it to position itself at polar-nonpolar interfaces.

The structure of cholesterol has been extensively studied, both in an anhydrous as well as a monohydrate form. Craven reported the crystal structure of cholesterol monohydrate, in crystals grown from acetone-water solution (Craven, B. M. Nature 260, 727-729 (1976)). The overall structure is a stacking of bilayers of thickness $d_{001}$=33.9 A°. The crystals are triclinic. The space group is PI, with reduced cell parameters a=12.39, b=12.41, c=34.36 A°, $\alpha$=91.9, p=98.1, $\gamma$=100.8°. Shieh et al. solved the structure of anhydrous cholesterol (Shieh, H. S. et al. Nature 267', 287-289 (1977)). They reported formation of lath-shaped crystals obtained by cooling a saturated acetone solution of cholesterol. The anhydrous crystal is also triclinic. The space group is PI, with reduced cell parameters a=14.00, b=33.71, c=10.46 A°, $\alpha$=94.5, $\beta$=90.0, $\gamma$=95.9°.

This example demonstrates a unique approach to growing crystals of cholesterol by compression of a monolayer at an air-water interface, near a metastable critical density point. The ordered structures produced by this technique were large (25-50 (µM in diameter), flat, highly ordered and diffracted electrons to atomic scale resolution. The results of this example, reveal a direct correlation between the degree of supersaturation in two-dimensions, beyond a metastable critical density point, and the cholesterol crystal nucleation process. The Langmuir technique was used as a tool to organize the amphiphilic cholesterol molecules at an air-water interface and subsequently compress them in two-dimensions to and beyond a critical density point.

Monolayers composed of a binary mixture containing cholesterol (>99%; Nu-Check-Prep, Inc., Elysian, Minn.), and 0.9 mole % of the fluorescent lipid probe L-α-Phosphatidylethanolamine-N-(lissamine rhodamine B sulfonyl) (Egg) (R-PE), or 1.6 mole % of the fluorescent lipid probe 1-Acyl-2-{12-{(7-nitro-2-1,3-benzoxadiazol-4-yl)amino}dodecanoyl}-sn-glycero-3-Phosphatidylethanolamine (NBD-PE) (both probes from Avanti Polar Lipids, Alabaster, Ala.), were formed at the air-water interface of the microscope mountable monolayer trough the Micro-Trough MT-100 (Ultrathin Film Technology, Ltd., Cambridge, Mass.). The trough was mounted on the stage of an Olympus IMT-2 microscope, equipped with the digital laser fluorescence video microscopy system described above. Fluorescence emission was excited with the 488 nm line of an air-cooled argon laser (Ion Laser Technology Systems, Salt Lake City, Utah). The fluorescent domains were imaged at the air-water interface, by using an Olympus DPlan ×10 (N.A. 0.25) or CDPlan ×40 (N.A. 0.50) ultralong working distance objectives. All monolayers were formed at ambient temperature (20±2° C.), over an ultra-pure water subphase. Ordered structures were transferred, from the air-water interface, to 200 mesh copper electron microscope grids coated with silicone oxide. Deposition of the ordered structures onto the substrates was monitored by fluorescence, throughout the transfer process. The degree of ordering in the ordered structures was analyzed by selected area electron diffraction of the deposited ordered structures. The electron diffraction studies were done on unstained specimen, at room temperature, by using the 1200 kV electron microscope facility at the Wadsworth Center, Albany, N.Y.

The cholesterol monolayer was compressed at a rate of 200 mm$^2$ per minute at the air-water interface. At low packing densities, and up to a characteristic limiting area around 36 Å$^2$ per molecule, the isotherm exhibits the characteristics of a highly compressible monolayer. The limiting area is to some extent affected by temperature fluctuations, the amount and composition of the fluorescent lipid probes in the binary mixture, as well as the errors involved in weighing and handling small quantities of material. The average limiting area reported in this study is consistent with a cross sectional area of 36.2 Å$^2$ per molecule of cholesterol, calculated by Craven from x-ray crystallographic analysis (Craven, B. M. Nature 260, 727-729 (1976)).

Further compression of the film, beyond the limiting area results no significant change in the film pressure. However, by fluorescence, formation of two different domain shapes was observed as a result of compression beyond the limiting area. At a critical density point an intermediary metastable phase was observed. This phase often appeared at an apparent area per molecule around 27 A, half way between the limiting area (around 36 Å$^2$ per molecule) and a characteristic area (around an apparent area at 18 Å$^2$ per molecule) where the molecules are expected to be stacked in a bilayer. The term "apparent area per molecule" is used here instead of "area per molecule" since at high packing densities, beyond the limiting area, the film is no longer monomolecular. Complex metastable patterns were produced around the critical density point. Further compression of the film, at a slow rate toward the characteristic bilayer area, produced a transformation in the shape of the patterns into plate-like parallelograms usually including a notch at some corners. The shape of the plate-like ordered structures is remarkably reminiscent of the shape of the crystals of cholesterol monohydrate. Under certain conditions, near the critical density point, a time-driven transformation of the metastable domains into the plate-like ordered structures was observed. These results indicate a direct correlation between the crystal nucleation process and the degree of super-saturation near the metastable critical density point. This relationship was further supported in control experiments where no crystals were formed if the film was compressed rapidly far beyond the metastable critical density point.

Electron diffraction analysis of the ordered structures transferred to a microscope grid, near the critical density point, provides evidence for the presence of highly ordered crystal domains of cholesterol, by exhibiting distinct diffraction spots. The diffraction pattern was taken from a ordered structure transferred to a silicon oxide grid near the critical density point around 27 Å$^2$ per molecule. The diffraction spots in the film were extremely resistant to beam damage. The calculated spacing from the diffraction spots in this pattern, was approximately a=13, b=17 Å. It is possible that the spots along the b axis originate from every other reciprocal lattice element in the repeat. If so, this would correspond to a doubling of the distance in the direct lattice parameters along the b axis; i.e. b=34 Å. In that case, the result will be remarkably consistent with the lattice parameters, reported by Shieh et al., for anhydrous cholesterol crystals; i.e. a=14.00, b=33.71 Å (Shieh, H. S. et al. *Nature* 267, 287-289 (1977)). FIG. 4-3 A,B shows bright field electron micrographs of the selected area.

It is quite unexpected that two-dimensional crystals of cholesterol to be formed by compressing a monolayer beyond a metastable critical density point. This method provides an ideal framework to extend the general theoretical derivations of Rein ten Wolde and Frenkel on enhancement of crystal nucleation by critical density fluctuations, to systems in two-dimensions (Rein ten Wolde, P. & Frenek, D. *Science* 211, 1975-1978 (1997)). A better theoretical understanding of the effects that underlie these empirical results may lead to a general rule for implying this powerful approach towards producing large and ordered crystals for other constituents of biological membranes, such as membrane proteins. Controlled fabrication of two-dimensional crystals of cholesterol, at an air-water interface, may provide further insight into the mechanism of cholesterol crystallization in vivo. This method is also expected to prove useful for screening drugs that promote or inhibit the cholesterol nucleation process.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference.

The invention claimed is:

1. A method for identifying whether a compound is a membrane protein modulator, the method comprising:
    contacting said compound with a two-dimensional ordered array of membrane proteins, said two-dimensional ordered array comprising a planar membrane under lateral compression;
    determining whether said compound can bind to said membrane proteins in said two-dimensional ordered array; and
    determining whether said compound can modulate activity of said membrane proteins in said two-dimensional ordered array,
    such that a membrane protein modulator is identified if said compound binds to and modulates activity of said membrane proteins in said two-dimensional ordered array.

2. The method of claim 1, wherein said two-dimensional ordered array is mounted on a solid support.

3. The method of claim 1, wherein said compound is selected from the group consisting of a small molecule, a nucleic acid, a carbohydrate, an antibody, a hormone, growth factor, a peptide, and a protein.

4. The method of claim 1, wherein said compound, said membrane proteins, or both comprise a label that enables binding to be detected, said label comprising a radio isotope, an enzyme, or a fluorescent label, and wherein determining whether said compound can bind to said membrane proteins in said two-dimensional ordered array comprises detecting said label.

5. The method of claim 1, wherein said two-dimensional array of membrane proteins comprises a lipid comprising a label that enables binding to be detected, said label selected from the group consisting of a radio isotope, an enzyme, and a fluorescent label, and wherein determining whether said compound can bind to said membrane proteins in said two-dimensional ordered array comprises detecting said label.

6. The method of claim 1, wherein said compound is screened for binding as an agonist, antagonist, inhibitor, or activator.

7. The method of claim 1, wherein determining whether said compound can modulate activity of said membrane proteins in said two-dimensional ordered array includes detecting a shape change of at least some of said membrane proteins.

8. The method of claim 7, wherein detecting a shape change of at least some of said membrane proteins includes detecting one or more of a conformational change in shape, multimerization of said membrane protein with itself, multimerization of said membrane protein with other membrane proteins, and fragmentation of said membrane protein.

9. The method of claim 1, wherein determining whether said compound can bind to said membrane proteins in said two-dimensional ordered array and/or determining whether said compound can modulate activity of said membrane proteins in said two-dimensional ordered array comprises performing one or more of thermal microanalysis, radio isotope detection, imaging, and diffraction analysis.

10. The method of claim 1, further comprising forming said two-dimensional ordered array of membrane proteins prior to contacting said compound with said two-dimensional ordered array of membrane proteins, said forming including:
    contacting a population of membrane proteins with a gas-aqueous interface; and
    laterally compressing said population to an appropriate packing density by planar membrane compression such that said two-dimensional ordered array of said membrane proteins is formed at said interface, wherein said appropriate packing density is below a critical density point.

* * * * *